(12) United States Patent
Zhang et al.

(10) Patent No.: US 10,632,080 B2
(45) Date of Patent: Apr. 28, 2020

(54) COMPOSITIONS AND METHODS TO IMPROVE NANOPARTICLE DISTRIBUTION WITHIN THE BRAIN INTERSTITIUM

(71) Applicant: The Johns Hopkins University, Baltimore, MD (US)

(72) Inventors: Clark Zhang, Sunnyvale, CA (US); Panagiotis Mastorakos, Charlottesville, VA (US); Jung Soo Suk, Baltimore, MD (US); Justin Hanes, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 15/759,465

(22) PCT Filed: Sep. 9, 2016

(86) PCT No.: PCT/US2016/050967
§ 371 (c)(1),
(2) Date: Mar. 12, 2018

(87) PCT Pub. No.: WO2017/044759
PCT Pub. Date: Mar. 16, 2017

(65) Prior Publication Data
US 2018/0271796 A1 Sep. 27, 2018

Related U.S. Application Data

(60) Provisional application No. 62/217,194, filed on Sep. 11, 2015.

(51) Int. Cl.
| | |
|---|---|
| *A61K 9/14* | (2006.01) |
| *A61K 9/51* | (2006.01) |
| *A61K 9/00* | (2006.01) |
| *A61K 49/00* | (2006.01) |
| *A61K 47/02* | (2006.01) |
| *A61P 25/00* | (2006.01) |

(52) U.S. Cl.
CPC .......... *A61K 9/5153* (2013.01); *A61K 9/0085* (2013.01); *A61K 9/5115* (2013.01); *A61K 9/5123* (2013.01); *A61K 9/5138* (2013.01); *A61K 9/5146* (2013.01); *A61K 47/02* (2013.01); *A61K 49/0032* (2013.01); *A61K 49/0093* (2013.01); *A61P 25/00* (2018.01)

(58) Field of Classification Search
None
See application file for complete search history.

(56) References Cited

U.S. PATENT DOCUMENTS

| | | | |
|---|---|---|---|
| 9,415,020 B2 * | 8/2016 | Ensign ................. | A61K 9/0034 |
| 2010/0015050 A1 * | 1/2010 | Panyam .................. | B82Y 5/00 |
| | | | 514/1.1 |
| 2010/0098767 A1 * | 4/2010 | Olbricht ................ | A61M 37/00 |
| | | | 424/489 |

OTHER PUBLICATIONS

Nance et al., "A Dense Poly(ethylene glycol) Coating Improves Penetration of Large Polymeric Nanoparticles within Brain Tissue" Sci Transl Med. Aug. 29, 2012; 4(149). (Year: 2012).*
Voges, et al., "Imaging-guided convection-enhanced delivery and gene therapy of glioblastoma", Ann Neurol, 54(4):479-87 (2003).
Yin, et al., "Convection-enhanced delivery improves distribution and efficacy of tumor-selective retroviral replicating vectors in a rodent brain tumor model", Cancer Gene Ther, 20(6):336-41 (2013).
Zhang, et al., "Interrelationships of the pia mater and the perivascular (Virchow-Robin) spaces in the human cerebrum", J Anat, 170:111-23 (1990).
Zhou, et al., "Highly penetrative, drug-loaded nanocarriers improve treatment of glioblastoma", PNAS, 110(29):11751-6 (2013).
Kroll, et al., "Increasing Volume of Distribution to the Brain with Interstitial Infusion: Dose, Rather Than Convection, Might Be the Most Important Factor", Neurosurgery, 38(4):746-52; discussion 752-4 (1996).
Kume-Kick, et al., "Independence of extracellular tortuosity and volume fraction during osmotic challenge in rat neocortex", J Physiol, 542(Pt 2):515-27 (2002).
Kunwar, et al., "Phase III randomized trial of CED of IL13-PE38QQR vs Gliadel wafers for recurrent glioblastoma", Neuro Oncol, 12(8):871-81 (2010).
Lang, et al., "Randomized controlled trial of intraputamenal glial cell line-derived neurotrophic factor infusion in Parkinson disease", Ann Neurol, 59(3):459-66 (2006).
Iliff, et al., "A paravascular pathway facilitates CSF flow through the brain parenchyma and the clearance of interstitial solutes, including amyloid β", Sci Transl Med, 4(147):147ra111 (2012).
Lochhead and Thorne, "Intranasal delivery of biologics to the central nervous system", Adv Drug Deliv Rev, 64(7):614-28 (2012).
MacKay, et al., "Distribution in brain of liposomes after convection enhanced delivery; modulation by particle charge, particle diameter, and presence of steric coating", Brain Res, 1035(2):139-53 (2005).
Mamot, et al., "Extensive distribution of liposomes in rodent brains and brain tumors following convection-enhanced delivery", J Neurooncol, 68(1):1-9(2004).
Mastakov, et al., Combined injection of rAAV with mannitol enhances gene expression in the rat brain Mol Ther, 3(2):225-32 (2001).
Nance, et al., "A dense poly(ethylene glycol) coating improves penetration of large polymeric nanoparticles within brain tissue", Sci Transl Med, 4(149):149ra119 (2012).
Nance, et al., "Brain-penetrating nanoparticles improve paclitaxel efficacy in malignant glioma following local administration", ACS Nano, 8(10):10655-64 (2014).
Nance, et al., "Non-invasive delivery of stealth, brain-penetrating nanoparticles across the blood-brain barrier using MRI-guided focused ultrasound", J Control Release, 189:123-32 (2014b).

(Continued)

*Primary Examiner* — Susan T Tran
(74) *Attorney, Agent, or Firm* — Pabst Patent Group LLP

(57) ABSTRACT

Improved distribution can be achieved by delivering nanoparticles possessing non-adhesive surfaces via CED in a hyperosmolar infusate solution. This delivery strategy minimizes the hindrances imposed by the brain extracellular matrix and reduces the concentration of therapeutic that is confined within perivascular spaces.

16 Claims, 6 Drawing Sheets

(56) References Cited

OTHER PUBLICATIONS

Neeves, et al., "Dilation and degradation of the brain extracellular matrix enhances penetration of infused polymer nanoparticles", Brain Res1180:121-32 (2007).

Papadopoulos, et al., "Aquaporin-4 facilitates reabsorption of excess fluid in vasogenic brain edema", FASEB J, 18(11):1291-3 (2004).

Pardridge, "Drug transport in brain via the cerebrospinal fluid", Fluids Barriers CNS, 8(1):7 (2011).

Patek, "The perivascular spaces of the mammalian brain", Anat. Rec., 88(1):1-24 (1944).

Preston, et al., "Capillary and arterial cerebral amyloid angiopathy in Alzheimer's disease: defining the perivascular route for the elimination of amyloid beta from the human brain", Neuropathol Appl Neurobiol, 29(2):106-17 (2003).

Saito, et al., "Tissue affinity of the infusate affects the distribution volume during convection-enhanced delivery into rodent brains: implications for local drug delivery", J Neurosci Methods, 154(1-2):225-32 (2006).

Salegio, et al., Distribution of nanoparticles throughout the cerebral cortex of rodents and non-human primates: Implications for gene and drug therapy Front Neuroanat, 8:9 (2014).

Sykova and Nicholson, "Diffusion in brain extracellular space", Physiol Rev, 88(4):1277-340 (2008).

Allard, et al., "Convection-enhanced delivery of nanocarriers for the treatment of brain tumors", Biomaterials, 30(12):2302-18 (2009).

Baker, et al., "Mechanisms of glioma formation: iterative perivascular glioma growth and invasion leads to tumor progression, VEGF-independent vascularization, and resistance to antiangiogenic therapy", Neoplasia, 16(7):543-61 (2014).Bala, et al., "PLGA nanoparticles in drug delivery: the state of the art", Crit Rev Ther Drug Carrier Syst, 21(5):387-422 (2004).

Bala, et al., "PLGA nanoparticles in drug delivery: the state of the art", Crit Rev Ther Drug Carrier Syst, 21(5):387-422 (2004).

Barua, et al., "Intrastriatal convection-enhanced delivery results in widespread perivascular distribution in a pre-clinical model", Fluids Barriers CNS, 9(1):2 (2012).

Bobo, et al., "Convection-enhanced delivery of macromolecules in the brain", PNAS, 91(6):2076-80 (1994).

Carare, et al., "Solutes, but not cells, drain from the brain parenchyma along basement membranes of capillaries and arteries: significance for cerebral amyloid angiopathy and neuroimmunology", Neuropathol Appl Neurobiol, 34(2):131-44 (2008).

Carty, et al., "Convection-enhanced delivery and systemic mannitol increase gene product distribution of AAV vectors 5, 8, and 9 and increase gene product in the adult mouse brain", J Neurosci Methods, 194(1):144-53 (2010).

Chen and Nicholson, "Changes in brain cell shape create residual extracellular space volume and explain tortuosity behavior during osmotic challenge", PNAS 97(15):8306-11 (2000).

Cuddapah, et al., "A neurocentric perspective on glioma invasion", Nat Rev Neurosci, 15(7):455-65 (2014).

Engelhardt and Coisne, "Fluids and barriers of the CNS establish immune privilege by confining immune surveillance to a two-walled castle moat surrounding the CNS castle", Fluids Barriers CNS, 8(1):4 (2011).

Foley, et al., "Real-time imaging of perivascular transport of nanoparticles during convection-enhanced delivery in the rat cortex", Ann Biomed Eng, 40(2):292-303 (2012).

Kamel, et al., "Hypertonic saline versus mannitol for the treatment of elevated intracranial pressure: a meta-analysis of randomized clinical trials", Crit Care Med, 39(3):554-9 (2011).

Krauze, et al., Effects of the perivascular space on convection-enhanced delivery of liposomes in primate putamen Exp Neurol, 196(1):104-11 (2005).

Krauze, et al., "Real-time visualization and characterization of liposomal delivery into the monkey brain by magnetic resonance imaging", Brain Res Brain Res Protoc, 16(1-3):20-6 (2005).

\* cited by examiner

COMPOSITIONS AND METHODS TO IMPROVE NANOPARTICLE DISTRIBUTION WITHIN THE BRAIN INTERSTITIUM

CROSS-REFERENCE TO RELATED APPLICATIONS

This application is a National Phase application under 35 U.S.C. 371 of PCT/US2016/050967, filed Sep. 9, 2016, which claims priority to and benefit of U.S. Provisional Application No. 62/217,194, filed Sep. 11, 2015, which is hereby incorporated herein by reference in its entirety.

STATEMENT REGARDING FEDERALLY SPONSORED RESEARCH OR DEVELOPMENT

This invention was made with government support under grant CA164789 awarded by the National Institutes of Health. The government has certain rights in the invention.

FIELD OF THE INVENTION

This invention is generally in the field of compositions and methods for the enhanced delivery of therapeutic, diagnostic, or prophylactic agents, and in particular, the delivering of these agents into the brain by facilitating their escape from perivascular spaces in order to achieve widespread volumes of distribution of these agents in brain interstitium.

BACKGROUND OF THE INVENTION

Many brain diseases are characterized by the presence of pathological cells or abnormal extracellular structures that are highly disseminated throughout the brain tissue. This necessitates the development of nanoparticle (NP) therapeutics that can achieve similarly extensive distribution (Allard, et al., Biomaterials, 2009, 30(12), 2302-18). Convection enhanced delivery (CED) is an effective delivery strategy to circumvent the blood brain barrier (BBB) and can theoretically achieve widespread NP distribution by harnessing a pressure driven bulk flow (Allard, et al., Biomaterials, 2009, 30(12), 2302-18; Bobo, et al., Proc Natl Acad Sci U.S.A, 1994, 91(6), 2076-80; Saito and Tominaga, Neurol Med Chir (Tokyo), 2012, 52(8), 531-8). However, recent advances in technological imaging have determined that administering a nanoparticle (NP) using CED still fails to achieve therapeutically favorable distribution (Krauze, et al., Exp Neurol, 2005, 196(1), 104-11). Intracranially administered NP travel through the brain interstitium, which comprises two distinct spaces: the intercellular space (ICS) and perivascular space (PVS). NP distribution in the ICS is limited by hindrances imposed by the extracellular matrix (ECM) components (Nance, et al., Sci Transl Med, 2012, 4(149), 149ra119). Moreover, the preferable flow of NP through, and subsequent confinement within, the low resistance, fluid-filled PVS reduces their ability to reach the target cells (Krauze, et al., Exp Neurol, 2005, 196(1), 104-11; Salegio, et al., Front Neuroanat, 2014, 8, 9). These revelations have shed light on prior terminated CED-based clinical trials that failed to meet their primary and secondary outcomes (Kunwar, et al., Neuro Oncol, 2010, 12(8), 871-81; Lang, et al., Ann Neurol, 2006, 59(3), 459-66) and have spurred the development of the next generation of NP systems optimized for CED (Zhou, et al., Proc Natl Acad Sci U.S.A, 2013, 110(29), 11751-6; Yin, et al., Cancer Gene Ther, 2013, 20(6), 336-41). An improved understanding of the mechanisms that contribute to poor NP distribution following CED will enable the development of specific strategies to overcome the aforementioned barriers and maximize therapeutic NP distribution within the brain parenchyma.

Conventionally designed NP, even when delivered via the bulk flow of CED, are often found localized solely near the point of administration and cannot travel away through the ICS (Voges, et al., Ann Neurol, 2003, 54(4), 479-87). Within the ICS, components of the brain ECM, which consists of a nanoporous network of interactive structures including proteoglycans and glycosaminoglycans (Sykova and Nicholson, Physiol Rev, 2008, 88(4), 1277-340), serve as a barrier that sterically and adhesively interacts with conventional NP following administration. It has previously been demonstrated that a NP up to 114 nm in diameter, if shielded with a dense layer of polyethylene glycol (PEG), can minimize interactions with the brain ECM and rapidly diffuse within the healthy brain ICS (Nance, et al., Sci Transl Med, 2012, 4(149), 149ra119). However, relying solely on diffusion to distribute therapeutic NP throughout the ICS achieves only sub-optimal therapeutic concentrations at farther distances (Allard, et al., Biomaterials, 2009, 30(12), 2302-18).

PVS are cerebrospinal fluid (CSF) filled canals surrounding large brain vessels and are responsible for the clearance of metabolites to maintain homeostasis in the brain (Iliff, et al., Sci Transl Med, 2012, 4(147), 147ra111). PVS have been shown to play an important role in numerous neurological diseases. In Alzheimer's disease, dysregulation of the PVS glymphatic system leads to widespread development of amyloid-β plaques (Iliff, et al., Sci Transl Med, 2012, 4(147), 147ra111; Preston, et al., Neuropathol Appl Neurobiol, 2003, 29(2), 106-17). Similarly, PVS, as paths of least resistance, have been implicated in facilitating the migration of malignant gliomas throughout the brain (Cuddapah, et al., Nat Rev Neurosci, 2014, 15(7), 455-65; Baker, et al., Neoplasia, 2014, 16(7), 543-61), thereby often leading to tumor recurrence.

Hence, preferential NP trafficking through the PVS, followed by radial escape through the glia limitans and into the ICS, may be exploited to chase the propagation of neurological disease. When administered into the brain, NP encounter a higher resistance when traveling through the ICS than through the PVS (Cuddapah, et al., Nat Rev Neurosci, 2014, 15(7), 455-65); therefore, significant quantities of infused NP have been visually confirmed to traffic through PVS (Krauze, et al., Exp Neurol, 2005, 196(1), 104-11; Barua, et al., Fluids Barriers CNS, 2012, 9(1), 2). Once localized in the PVS, NPs remain sequestered due to the glia limitans, the anatomical barrier that separates the PVS and ICS (Engelhardt and Coisne, Fluids Barriers CNS, 2011, 8(1), 4). More importantly, NP accumulation and entrapment in PVS occurs following all available delivery strategies to the brain, including administrations using intranasal, intracisternal, or intrathecal routes (Salegio, et al., Front Neuroanat, 2014, 8, 9; Foley, et al., Ann Biomed Eng, 2012, 40(2), 292-303; Lochhead and Thorne, Adv Drug Deliv Rev, 2012, 64(7), 614-28). Given that NP confinement in PVS has been suggested to lead to a reduction in therapeutic efficacy in clinical trials (Barua, et al., Fluids Barriers CNS, 2012, 9(1), 2; Krauze, et al., Brain Res Brain Res Protoc, 2005, 16(1-3), 20-6), an effective strategy to reduce PVS sequestration is essential.

It is therefore an object of the present invention to provide a composition with improved brain intercellular space distribution.

It is another object of the present invention to provide shielded NPs in a hyperosmotic solution, which possess improved brain intercellular space distribution, by virtue of enhanced escape of the NPs from PVS, increased diffusion within brain ECM, or both.

It is a further object of the present invention to provide a method for delivering a composition with improved brain intercellular space distribution, by virtue of the osmotic modulation of the brain tissue in order to minimize the hindrances of the brain ECM and preferable NP accumulation in PVS.

It is another object of the present invention to provide a method for delivering shielded NPs in a hyperosmotic solution, which possess improved brain intercellular space distribution, by virtue of enhanced escape of the NPs from PVS, increased diffusion within brain ECM, or both.

SUMMARY OF THE INVENTION

Compositions and methods for improved distribution of nanoparticles in brain interstitium have been developed. The compositions contain nanoparticles in a hyperosmolar solution. The nanoparticle contains a first polymer, and a second hydrophilic, neutrally charged polymer that is linked to the first polymer to form a conjugate. In a preferred embodiment, the first polymer is poly(lactide-co-glycolic acid). The surface of the nanoparticle is coated with a dense coating of the hydrophilic, neutrally charged polymer, or other coating agent. The hydrophilic or neutrally charged polymer preferably includes polyethylene glycol ("PEG"), poloxomers (polyethylene oxide block copolymers), polysorbate 80 or combinations thereof. In a preferred embodiment, the dense coating is PEG. The dense coating enhances the distribution of the nanoparticles within brain interstitium by decreasing the adhesion of the nanoparticles with components of the brain extracellular matrix (ECM). The nanoparticles are preferably less than 200 nm, more preferably less than 150, most preferably less than 100 nm. In the examples, the nanoparticles have a diameter of less than or equal to 114 nm, 80 nm or 60 nm.

In some embodiments the PEG is branched. Branching enhances the density of the polyethylene glycol conjugated to the polymer. In some embodiments the polyethylene glycol has a molecular weight between 1,000 Daltons and 10,000 Daltons, such as 5,000 Daltons.

The hyperosmolar solution is formed from a solution such as saline solutions, and mannitol solutions. The hyperosmolar solution enhances the distribution of the nanoparticles within brain interstitium by increasing the pore sizes within the ECM of the brain, thereby facilitating the diffusion of the nanoparticles within the brain interstitium. In preferred embodiments, the hyperosmolar solution is saline. In a more preferred embodiment, the hyperosmolar solution is a 3% solution of saline. The examples show that the combined reduction of adhesion and increase in the pore sizes within the ECM improves the distribution of the nanoparticles away from the point of administration, and allows the escape of the nanoparticles form the perivascular spaces of the brain.

Dosage formulations for the delivery of a therapeutic, prophylactic or diagnostic agent to the brain are also disclosed. The formulations include a therapeutically effective amount of nanoparticles densely coated with PEG and a pharmaceutically acceptable excipient for delivery into the brain. The nanoparticles can be formulated for direct or indirect injection into the brain.

Methods of using the compositions include, but are not limited to, administering the composition via convention enhanced delivery.

The compositions and methods can be used to improve the delivery of any one of therapeutic, prophylactic and diagnostic agents, to treat one or more symptoms of various disorders or diseases of the brain, including brain cancer, Alzheimer's disease, Parkinson's disease, Huntington's disease, stroke, acute and chronic traumatic and pain syndromes.

BRIEF DESCRIPTION OF THE DRAWINGS

(FIG. 2A) and mean squared displacement (<MSD>) of PS-PEG in rodent brain slices that were incubated in infusate solutions of varying salinity (FIG. 2B). N>100 NP tracked per sample, N=4 rodent samples. * $P<0.05$ denotes statistical significance. (B) Vd of PS-PEG and PS-COOH determined using image based MATLAB quantification methods. * $p<0.05$ denotes statistical significance.

(FIGS. 3A-3C). The presence of NP fluorescence corresponding to PS-PEG is detected up to 100 μm away from the PVS of the striate artery when delivered in hyperosmolar 3% saline solution. PS-COOH do not effectively escape from PVS regardless of osmolarity of infusate solution. At least N=3 striate vessels quantified for each condition. Percent coverage of PS-PEG and PS-COOH fluorescence within the ICS calculated using image based MATLAB quantification (FIG. 3D). Significantly higher PS-PEG coverage is detected when infused in 3% saline as compared to all other conditions. Statistical significance denoted by * $p<0.05$.

FIG. 4A shows the quantified Vd of PLGA-PEG and PLGA in mouse striatum. Inset depicts the low Vd of PLGA. * $p<0.05$ denotes statistical significance. FIG. 4B is a graph showing the improved perivascular escape of PLGA-PEG occurs when administered in 3% saline as opposed to 0.9% saline. FIG. 4C is a graph of the percent coverage of PLGA-PEG fluorescence within the brain ICS calculated using image based MATLAB quantification. Significantly higher PLGA-PEG are found in the ICS when infused in 3% saline as compared to 0.9% saline. Statistical significance denoted by * $p<0.05$.

DETAILED DESCRIPTION OF THE INVENTION

I. Definitions

Figure 1A:
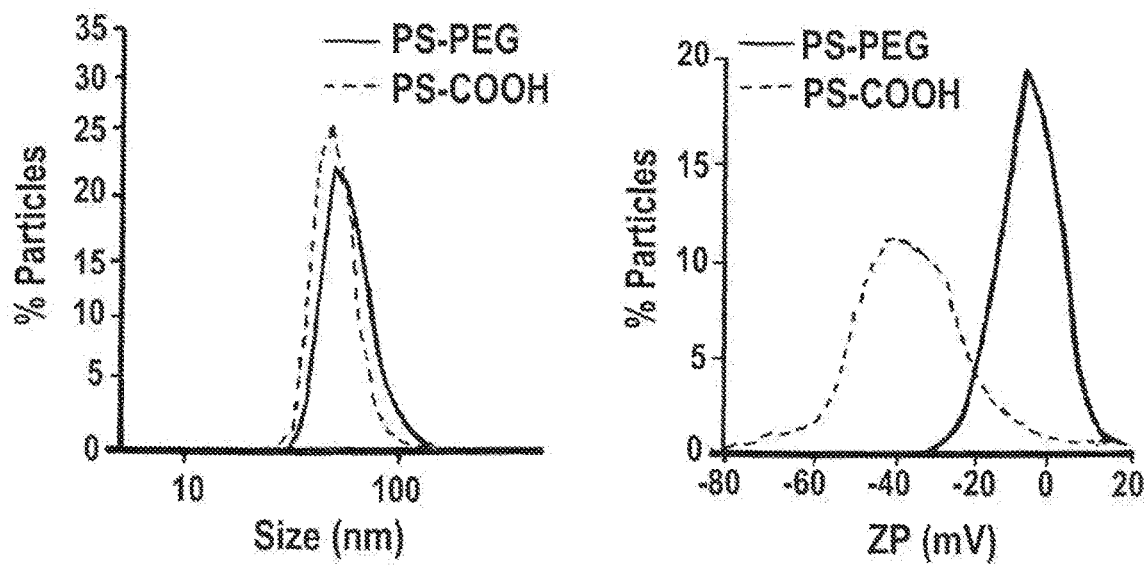
FIGS. 1A and 1B are graphs of the physicochemical characterization of model polystyrene based nanoparticles (FIG. 1A) and quantitative volume of distribution (Vd) of PS-PEG and PS-COOH NP when infused into the brain at varying concentrations (FIG. 1B). Statistical significance denoted by * $p<0.05$.

The terms "biocompatible" as used herein refers to one or more materials that are neither themselves toxic to the host (e.g., an animal or human), nor degrade (if the polymer degrades) at a rate that produces monomeric or oligomeric subunits or other byproducts at toxic concentrations in the host.

The term "biodegradable" as used herein means that the materials degrades or breaks down into its component subunits, or digestion, e.g., by a biochemical process, of the polymer into smaller, non-polymeric subunits.

The term "corresponding particle" or "reference particles" as used herein refers to a particle that is substantially identical to another particle to which it is compared, but typically lacking a surface modification to promote transport differences through the pores in the ECM of the brain. A corresponding particle is typically of similar material, density, and size as the particle to which it is compared. In certain embodiments, a corresponding particle is a particle that does not have a dense coating of PEG or other coating agent. In certain embodiments, a comparable particle is a particle that is not formed of a blended mixture containing free polymer and polymer conjugated to PEG. In certain embodiments, a corresponding particle is of similar material as the particle to which it is compared, but smaller or larger in size.

The term "densely coated particle" refers to a particle that is modified to specifically enhance the density of coating agent at the surface of the particle, for example, relative to a reference particle. In some embodiments, a densely coated particle is formed from a ratio of PEG to polymer that is sufficient to alter the physicochemical properties of the particle relative to a less densely coated, or non-coated particle. In some embodiments, the density of coating agent is sufficient to completely mask the charge of the particle, resulting in a near neutral charge and near neutral zeta potential value and colloidal stability in physiological solutions. In a particular embodiment, a densely coated particle is achieved using branched PEG or branched polymer, wherein the branching enhances the ratio of PEG to polymer as compared to a reference particle that does not contain a branched polymer or branched polyethylene glycol.

The term "hyperosmolar," is art-recognized, and refers to a solution that has a higher osmole per liter, compared to another solution, most typically referring to a saline solution of less than 0.9% saline. In one embodiment, another solution is the cytoplasm of brain cells.

The term "iso-osmolar," is art-recognized, and refers to a solution that has an equal osmole per liter, compared to another solution. In one embodiment, another solution is the cytoplasm of brain cells.

The term "hypo-osmolar," is art-recognized, and refers to a solution that has a lower osmole per liter, compared to another solution. In one embodiment, another solution is the cytoplasm of brain cells.

The term "diameter" is art-recognized and is used herein to refer to either of the physical diameter or the hydrodynamic diameter. The diameter of an essentially spherical particle may refer to the physical or hydrodynamic diameter. The diameter of a non-spherical particle may refer preferentially to the hydrodynamic diameter. As used herein, the diameter of a non-spherical particle may refer to the largest linear distance between two points on the surface of the particle. When referring to multiple particles, the diameter of the particles typically refers to the average diameter of the particles.

"Sustained release" as used herein refers to release of a substance over an extended period of time in contrast to a bolus type administration in which the entire amount of the substance is made biologically available at one time.

The term "microspheres", "microparticles", and "microcapsules are used interchangeably unless otherwise stated. These have a size between about one up to about 1000 microns. In general, "microcapsules," have a core of a different material than the shell material. A microparticle may be spherical or nonspherical and may have any regular or irregular shape. If the structures are less than about one micron in diameter, then the corresponding art-recognized terms "nanosphere," "nanocapsule," and "nanoparticle" may be utilized. In certain embodiments, the nanospheres, nanocapsules and nanoparticles have an average diameter of about 200 nm, 100 nm, or less than 100 nm, such as 50 nm, or 10 nm.

A composition containing microparticles or nanoparticles may include particles of a range of particle sizes. In certain embodiments, the particle size distribution may be uniform, e.g., within less than about a 20% standard deviation of the median volume diameter, and in other embodiments, still more uniform, e.g., within about 10% of the median volume diameter.

The term "surfactant" refers to an agent that lowers the surface tension of a liquid.

The terms "incorporated" and "encapsulated" refer to incorporating, formulating, or otherwise including an active agent into and/or onto a composition that allows for release, such as sustained release, of such agent in the desired application. The terms contemplate any manner by which a therapeutic agent or other material is incorporated into a polymer matrix, including chemically or physically couple, in physical admixture, or enveloping the agent in a coating layer.

The term "treating" refers to preventing or alleviating one or more symptoms of a disease, disorder or condition. Treating the disease or condition includes ameliorating at least one symptom of the particular disease or condition, even if the underlying pathophysiology is not affected, such as treating the pain of a subject by administration of an analgesic agent even though such agent does not treat the cause of the pain.

The phrase "pharmaceutically acceptable" refers to compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier" refers to pharmaceutically acceptable materials, compositions or vehicles, such as a liquid or solid filler, diluent, solvent or encapsulating material involved in carrying or transporting any subject composition, from one organ, or portion of the body, to another organ, or portion of the body. Each carrier must be "acceptable" in the sense of being compatible with the other ingredients of a subject composition and not injurious to the patient.

The phrase "therapeutically effective amount" refers to an amount of the therapeutic agent that produces some desired effect at a reasonable benefit/risk ratio applicable to any medical treatment. The effective amount may vary depending on such factors as the disease or condition being treated, the particular targeted constructs being administered, the size of the subject, or the severity of the disease or condition. One of ordinary skill in the art may empirically determine the effective amount of a particular compound without necessitating undue experimentation.

II. Compositions

Compositions of a hyperosmolar solution containing nanoparticles with a dense surface coating of hydrophilic and neutrally charged polymer such as polyethylene glycol (PEG) or polyethylene glycol-polyoxyethylene block copolymer known as poloxamer such as a PLURONIC® (referred to collectively as "PEGylated particles"), which are capable of rapid diffusion and widespread distribution in brain tissue are disclosed.

A. Nanoparticles

The nanoparticles can be polymeric particles, nanogels, hybrid lipid-polymer particles, nanogels, nanolipogel-based and dendrimers. In some embodiments the nanoparticles may be solid or hollow and may comprise one or more layers. In some embodiments, each layer has a unique composition and unique properties relative to the other layer(s). The nanoparticles can be biodegradable or non-biodegradable. In a preferred embodiment, the nanoparticles are polymeric, i.e., polymeric nanoparticles. In the most preferred embodiment, the polymeric nanoparticles contain a dense surface coating of a hydrophilic and neutrally charged polymer.

1. Coating Agents

Nanoparticles, coated with one or more materials that promote diffusion of the particles through the ECM in the brain by reducing interactions between the particles and brain tissue (e.g., surface altering agents) are disclosed. Examples of the surface-altering agents include, but are not limited to, polyethylene glycol ("PEG"), poloxomers (polyethylene oxide block copolymers), polysorbate 80 and combinations thereof. In some embodiments, the coating agent is linked to the nanoparticle after the nanoparticle has been formed. In another embodiment, the coating agent is linked to a polymer that is used to form the core of the nanoparticle, before the nanoparticle is formed.

A preferred coating agent is poly(ethylene glycol), also known as PEG. PEG may be employed to reduce adhesion in brain ECM in certain configurations, e.g., wherein the length of PEG chains extending from the surface is controlled (such that long, unbranched chains that interpenetrate into the ECM are reduced or eliminated). For example, linear high MW PEG may be employed in the preparation of particles such that only portions of the linear strands extend from the surface of the particles (e.g., portions equivalent in length to lower MW PEG molecules). Alternatively, branched high MW PEG may be employed. In such embodiments, although the molecular weight of a PEG molecule may be high, the linear length of any individual strand of the molecule that extends from the surface of a particle would correspond to a linear chain of a lower MW PEG molecule.

Representative PEG molecular weights in daltons (Da) include 300 Da, 600 Da, 1 kDa, 2 kDa, 3 kDa, 4 kDa, 5 kDa, 6 kDa, 8 kDa, 10 kDa, 15 kDa, 20 kDa, 30 kDa, 50 kDa, 100 kDa, 200 kDa, 500 kDa, and 1 MDa. In preferred embodiments, the PEG has a molecular weight of about 5,000 Daltons. PEG of any given molecular weight may vary in other characteristics such as length, density, and branching. In one embodiment, a coating agent is methoxy-PEG-N-hydroxysuccinimide with a MW of 5 kDa (mPEG-NHS 5 kDa). In a particular embodiment, a coating agent is methoxy-PEG-amine, with a MW of 5 kDa.

In alternative embodiments, the coating is a poloxamer such as the polyethylene glycol-polyethylene oxide block copolymers marketed as PLURONICs®.

In some embodiments, the coating is linked covalently or non-covalently with the core of the nanoparticle to form a conjugate. In some embodiments, the covalent linkage between the coating and the core of the nanoparticle is direct. In other embodiments, the coating is linked to the core of the nanoparticle indirectly through a linker moiety. In some embodiments, the non-covalent linkage is mediated by affinity interactions, metal coordination, physical adsorption, host-guest interactions, hydrophobic interactions, π-stacking, hydrogen bonding, van der Waals' interactions, or combinations thereof. In preferred embodiments, the coating agent is linked covalently to the core of the nanoparticle.

In preferred embodiments the nanoparticles are coated with PEG or other coating agent at a density that optimizes rapid diffusion through the brain parenchyma. The density of the coating can be varied based on a variety of factors including the material and the composition of the particle.

The amount of the PEG or other coating agent is expressed as a molar ratio of PEG or other coating agent to the core polymer. The molar ratio of PEG or other coating agent to the core polymer is selected such that the nanoparticles display rapid diffusion through the brain parenchyma, as compared to a corresponding particle that does not have a dense coating of polyethylene glycol or other coating agent.

In one embodiment, the density of the PEG or other coating agent is at least 0.001, 0.002, 0.005, 0.01, 0.02, 0.05, 0.1, 0.2, 0.5, 1, 2, 5, 10, 20, 50, or 100 units per $nm^2$.

In another embodiment, the amount of the PEG or other coating agent is expressed as a percentage of the mass of the particle. In a particular embodiment, the mass of the PEG or other coating agent is at least 1/10,000, 1/7500, 1/5000, 1/4000, 1/3400, 1/2500, 1/2000, 1/1500, 1/1000, 1/500, 1/250, 1/200, 1/150, 1/100, 1/75, 1/50, 1/25, 1/20, 1/5, 1/2, or 9/10 of the mass of the particle. In a further embodiment, the weight percent of the PEG or other coating agent is at least 80%, 81%, 82%, 83%, 84%, 85%, 86%, 87%, 88%, 89%, 90%, 91%, 92%, 93%, 94%, 95%, or greater.

In yet another embodiment, the amount of the PEG or other coating agent is expressed as a percentage of the mass of the conjugate of PEG- or other coating agent-core polymer. In some embodiments the weight percent of the PEG or other coating agent in the conjugate is between about 10 wt % and about 90 wt %.

2. Core Polymer

Any number of biocompatible polymers can be used to prepare the nanoparticles. The polymer can be a linear polymer or a branched polymer in order to enhance the capacity of the polymer to conjugate to a coating agent such as PEG. In some embodiments, the biocompatible polymer(s) is biodegradable. In some embodiments, the biocompatible, biodegradable polymer is amphiphilic. In another embodiment, the biocompatible, biodegradable polymer is hydrophobic. Copolymers of two or more polymers, including block copolymers, random copolymers, or both, may also be employed to make the polymeric particles.

Examples of preferred biodegradable polymers include poly(hydroxy acids), including polymers of hydroxy acids lactic acid and glycolic acid, and copolymers of these hydroxy acids with PEG; polyanhydrides; poly(ortho)esters; polyurethanes; poly(butyric acid); poly(valeric acid); poly (lactide-co-caprolactone); poly(amine-co-ester); blends and copolymers thereof. In preferred embodiments, the particles are composed of one or more polyesters.

In some embodiments, the one or more polyesters are hydrophobic.

For example, particles can contain one more of the following polyesters: homopolymers including glycolic acid units, referred to herein as "PGA", and lactic acid units, such as poly-L-lactic acid, poly-D-lactic acid, poly-D,L-lactic acid, poly-L-lactide, poly-D-lactide, and poly-D,L-lactide, collectively referred to herein as "PLA", and caprolactone units, such as poly(ε-caprolactone), collectively referred to herein as "PCL"; and copolymers including lactic acid and glycolic acid units, such as various forms of poly(lactic acid-co-glycolic acid) and poly(lactide-co-glycolide) characterized by the ratio of lactic acid:glycolic acid, collectively referred to herein as "PLGA"; and polyacrylates, and derivatives thereof.

Additional hydrophobic polymers include, but are not limited to, polyhydroxyalkanoates, poly(phosphazenes), polycarbonates, polyamides, polyesteramides, poly(alkylene alkylates), hydrophobic polyethers, polyetheresters, polyacetals, polycyanoacrylates, polyacrylates, polymethylmethacrylates, polysiloxanes, polyketals, polyhydroxyvalerates, polyalkylene oxalates, polyalkylene succinates, and copolymers thereof.

In some embodiments, the polymers are amphiphilic containing a hydrophilic and a hydrophobic polymer described above.

Suitable hydrophilic polymers include, but are not limited to, hydrophilic polypeptides, such as poly-L-glutamic acid, gamma-polyglutamic acid, poly-L-aspartic acid, poly-L-serine, or poly-L-lysine, poly(alkylene glycols) such as polyethylene glycol (PEG), poly(propylene glycol) and copolymers of ethylene glycol and propylene glycol, poly (oxyethylated polyol), poly(olefinic alcohol), polyvinylpyrrolidone), poly(hydroxyalkylmethacrylamide), poly(hydroxyalkylmethacrylate), poly(saccharides), poly (vinyl alcohol), as well as copolymers thereof. In some embodiments, the hydrophilic polymer is PEG.

Exemplary amphiphilic polymers also include copolymers of polyethylene glycol (PEG) and the aforementioned polyesters, such as various forms of PLGA-PEG or PLA-PEG copolymers. In certain embodiments, the PEG region is covalently associated with the polymer to yield "PEGylated polymers", optionally coupled by a cleavable linker. Alginate polymers may also be used.

In a preferred embodiment, the core polymer is PLGA. PLGA is a safe, FDA approved polymer.

Examples of polymers that can be used to form a non-biodegradable nanoparticle include polystyrene, ethylene vinyl acetate, poly(meth)acrylic acid, polyamides, copolymers and mixtures thereof.

In polymer chemistry, branching occurs by the replacement of a substituent, e.g., a hydrogen atom, on a monomer subunit, by another covalently bonded chain of that polymer; or, in the case of a graft copolymer, by a chain of another type. Branching may result from the formation of carbon-carbon or various other types of covalent bonds. Branching by ester and amide bonds is typically by a condensation reaction, producing one molecule of water (or HCl) for each bond formed.

The branching index measures the effect of long-chain branches on the size of a macromolecule in solution. It is defined as $g=<sb^2>/<sl^2>$, where sb is the mean square radius of gyration of the branched macromolecule in a given solvent, and sl is the mean square radius of gyration of an otherwise identical linear macromolecule in the same solvent at the same temperature. A value greater than 1 indicates an increased radius of gyration due to branching.

In preferred embodiments, copolymers of PEG or derivatives thereof with any of the polymers described above may be used to make the polymeric particles. In certain embodiments, the PEG or derivatives may locate in the interior positions of the copolymer. Alternatively, the PEG or derivatives may locate near or at the terminal positions of the copolymer. In certain embodiments, the nanoparticles are formed under conditions that allow regions of PEG to phase separate or otherwise locate to the surface of the particles. The surface-localized PEG regions alone may perform the function of, or include, a surface-altering agent.

3. Nanoparticle Properties

As shown in the examples, the disclosed nanoparticles densely-coated with PEG or other coating agent through the pores of the ECM of the brain at a greater rate of diffusivity than a reference nanoparticle, such as an uncoated particle, e.g., uncoated carboxylated polystyrene particle.

i. Particle Volume of Distribution

Following administration, the disclosed nanoparticles densely-coated with PEG or other coating agent distribute within brain ICS with a volume of distribution (Vd) that is at 1.3, 2, 5, 10, 20, 30, 50, 60, 80, 100, 125, 150, 200, 250, 500, 600, 750, 1000, 1500, 2000, 2500, 3000, 4000, 5000, 10000- or greater fold higher than a reference particle. In some embodiments, the volume of distribution is measured by determining the fluorescence of fluorescently-labeled nanoparticles in slices of brain tissue with a certain distance from the injection site post-administration. The brain slice images are quantified for fluorescent distribution of nanoparticles by running confocal laser scanning microscope images of the brain slices through a custom MATLAB script, with a 10% maximum fluorescent intensity threshold. Fluorescent distribution of NP in the ventricles or white matter tracts are avoided and not included in the quantification. The area of distribution calculated from each slice is multiplied by the thickness of the brain slice and summated across all images to obtain a total volume of distribution.

In particular embodiments, the Vd of the coated particles is about six- to seven-fold higher than that of a reference particle. In other embodiments, the Vd of the coated particles is 10.7-fold, 6.8-fold, 5.8-fold, 3.6-fold and 1.3-fold higher than that of a reference particle.

ii. Particle Diffusivity

The disclosed nanoparticles densely-coated with PEG or other coating agent pass through the pores of the ECM of the brain at a rate of diffusivity that is at least 5, 10, 20, 30, 50, 60, 80, 100, 125, 150, 200, 250, 500, 600, 750, 1000, 1500, 2000, 2500, 3000, 4000, 5000, 10000- or greater fold higher than a reference particle.

The transport rates of the particles can be measured using a variety of techniques in the art. In one embodiment, the rate of diffusion is measured by geometric ensemble mean squared displacements (MSD). In a particular embodiment, the particles may diffuse through the pores of the ECM of the brain with an MSD that is at least 5, 10, 20, 30, 50, 60, 80, 100, 125, 150, 200, 250, 500, 600, 750, 1000, 1500, 2000, 2500, 3000, 4000, 5000, 10000- or greater fold higher than a reference particle.

In other embodiments, the disclosed nanoparticles densely-coated with PEG or other coating agent diffuse through the pores of the ECM of the brain at a rate approaching the rate of diffusivity at which the particles diffuse through water. In some embodiments, the rate of diffusivity is at least $\frac{1}{1000}$, $\frac{1}{800}$, $\frac{1}{700}$, $\frac{1}{600}$, $\frac{1}{500}$, $\frac{1}{400}$, $\frac{1}{250}$, $\frac{1}{200}$, $\frac{1}{150}$, $\frac{1}{100}$, $\frac{1}{75}$, $\frac{1}{50}$, $\frac{1}{25}$, $\frac{1}{10}$, $\frac{1}{7}$, $\frac{1}{5}$, $\frac{1}{2}$, or 1 times the rate of diffusivity of the particle in water under identical conditions. For example, at a time scale of 1 s, the rates of diffusion of unmodified or reference particles can be slower in brain tissue than the same particles in water.

The density of coating of PEG or other material can affect the diffusion of nanoparticle within brain ICS. In some embodiments the MSD at 1 sec of densely PEGylated particles is at least 1.5-fold higher than that of a reference particle. In a particular embodiment, the densely PEGylated particle diffuse to a distance of at least 0.5 mm, 1.0 mm and 1.5 mm in the ICS, while the reference particle is not observed in the ICS.

The heterogeneity in particle transport rates can also be evaluated by examining the distribution of individual particle diffusivities over a particular time period, e.g., 1 s. In one embodiment, at least 15%, 20%, 25%, 30%, 35%, 40%, 45%, 50%, 55%, 60%, 65%, 70%, 75%, 80%, or greater of coated particles of a given average particle size are classified as diffusive. This value is affected by the selection of the polymer. For example, PLGA nanoparticles will typically have particle diffusivities of about 50% while 80% or greater of polystyrene nanoparticles will be diffusive. This is in accordance with the definition of a diffusive nanoparticle as one that exhibits log(MSD)>−1.

iii. Electro-kinetic Potential

The presence of the PEG or coating agent can affect the zeta-potential of the particle. In one embodiment, the zeta potential of the particles is between −100 mV and 10 mV, between −50 mV and 10 mV, between −25 mV and 10 mV, between −20 mV and 5 mV, between −10 mV and 10 mV, between −10 mV and 5 mV, between −5 mV and 5 mV, or between −2 mV and 2 mV. In a preferred embodiment, the surface charge is near neutral.

iv. Particle Size

In some embodiments, the disclosed nanoparticles densely-coated with PEG or other coating agent have an average diameter equal to or smaller than the pores in the ECM of the brain. In particular embodiments, the particles have an average diameter up 114 nm, less than 100 nm, from about 30 to about 80 nm. In some embodiments the shielded nanoparticles have an average diameter from about 71.1±1 nm to about 75±3 nm. In other embodiments, the shielded nanoparticles have an average diameter from about 58±0.2 nm to about 62±0.5 nm. Particle size can be measured using any technique known in the art, for example using dynamic light scattering.

In another embodiment, the particles have an average diameter such that a majority of the particles do not become localized within perivascular spaces.

In certain embodiments the nanoparticles release an effective amount of the therapeutic, diagnostic or prophylactic agent over a period of at least 10 minutes, 20 minutes, 30 minutes, one hour, two hours, hour hours, six hours, ten hours, one day, three days, seven days, ten days, two weeks, one month, or longer.

v. Toxicity

The in vitro or in vivo toxicity of disclosed shielded nanoparticles densely-coated with PEG or other coating agents can be assessed using any technique known in the art, such as cell viability assays, or observing the behavior of subjects to which the nanoparticles have been administered. Preferably, nanoparticles which are densely-coated with PEG or other coating agents are less toxic than the same non-coated particles. Some particles may not be pegylated however, such as most of the polystyrene and PGLA-based nanoparticles. The toxicity of the nanoparticles can be dependent upon the cell-type or tissue-type and can depend upon the concentration of the nanoparticles, the osmolarity of the infusate solution, or both. In some embodiments toxicity is considered low when no significant cellular toxicity or inflammation is observed in the vicinity of the site administration or distal to the site of administration. Toxicity is measured by those skilled in the art by measuring cell viability, inflammation, and in the case of animals, normal weight gain and alert behavior. Signs of typical neurotoxicity include behavioral changes such as hunched postures, gait abnormalities, lethargy, ataxia, and/or convulsions. None of these symptoms were observed upon close monitoring of animal behavior.

4. Therapeutic, Prophylactic or Diagnostic Agents

In some embodiments, the particles have encapsulated therein, dispersed therein, and/or covalently or non-covalently associate with the surface one or more therapeutic agents. The therapeutic agent can be a small molecule, protein, polysaccharide or saccharide, nucleic acid molecule and/or lipid.

Any protein can be formulated, including recombinant, isolated, or synthetic proteins, glycoproteins, or lipoproteins. These may be antibodies (including antibody fragments and recombinant antibodies), enzymes, growth factors or hormones, immunomodifiers, antiinfectives, antiproliferatives, or other therapeutic, prophylactic, or diagnostic proteins. In certain embodiments, the protein has a molecular weight greater than about 150 kDa, greater than 160 kDa, greater than 170 kDa, greater than 180 kDa, greater than 190 kDa or even greater than 200 kDa. In certain embodiments, the protein can be a PEGylated protein.

Exemplary classes of small molecule therapeutic agents include, but are not limited to, analgesics, anti-inflammatory drugs, antipyretics, antidepressants, antiepileptics, antiopsychotic agents, neuroprotective agents, anti-proliferatives, such as anti-cancer agent, anti-infectious agents, such as antibacterial agents and antifungal agents, antihistamines, antimigraine drugs, antimuscarinics, anxioltyics, sedatives, hypnotics, antipsychotics, bronchodilators, anti-asthma drugs, cardiovascular drugs, corticosteroids, dopaminergics, electrolytes, gastro-intestinal drugs, muscle relaxants, nutritional agents, vitamins, parasympathomimetics, stimulants, anorectics and anti-narcoleptics.

In some embodiments, the agent is one or more nucleic acids. The nucleic acid can alter, correct, or replace an endogenous nucleic acid sequence. The nucleic acid can be used to treat cancers, correct defects in genes in pulmonary diseases and metabolic diseases affecting lung function, for example, to treat Parkinsons and ALS where the genes reach the brain through nasal delivery.

Gene therapy is a technique for correcting defective genes responsible for disease development. A normal gene may be inserted into a nonspecific location within the genome to replace a nonfunctional gene. This approach is most common. An abnormal gene could be swapped for a normal gene through homologous recombination. The abnormal gene could be repaired through selective reverse mutation, which returns the gene to its normal function. The regulation (the degree to which a gene is turned on or off) of a particular gene could be altered.

The nucleic acid can be a DNA, RNA, a chemically modified nucleic acid, or combinations thereof. For example, methods for increasing stability of nucleic acid half-life and resistance to enzymatic cleavage are known in the art, and can include one or more modifications or substitutions to the nucleobases, sugars, or linkages of the polynucleotide. The nucleic acid can be custom synthesized to contain properties that are tailored to fit a desired use. Common modifications include, but are not limited to use of locked nucleic acids (LNAs), unlocked nucleic acids (UNAs), morpholinos, peptide nucleic acids (PNA), phosphorothioate linkages, phosphonoacetate linkages, propyne analogs, 2'-O-methyl RNA, 5-Me-dC, 2'-5' linked phosphodiester linkage, Chimeric Linkages (Mixed phosphorothioate and phosphodiester linkages and modifications), conjugation with lipid and peptides, and combinations thereof.

Exemplary diagnostic materials include paramagnetic molecules, fluorescent compounds, magnetic molecules, and radionuclides. Suitable diagnostic agents include, but are not limited to, x-ray imaging agents and contrast media. Radionuclides also can be used as imaging agents. Examples of other suitable contrast agents include gases or gas emitting compounds, which are radioopaque. Liposomes can further include agents useful for determining the location of administered particles. Agents useful for this purpose include fluorescent tags, radionuclides and contrast agents.

In preferred embodiment, anti-infectives include antibiotics such as tobramycin, colistin, or aztreonam; and anti-inflammatory agents include erythromycin, azithromycin, and clarithromycin. Nanoparticles may also be used for the delivery of chemotherapeutic agents, and anti-proliferative agents.

For those embodiments where the one or more therapeutic, prophylactic, and/or diagnostic agents are encapsulated, the percent drug loading is from about 1% to about 80%, from about 1% to about 50%, from about 1% to about 40% by weight, from about 1% to about 20% by weight, or from about 1% to about 10% by weight.

5. Targeting Moieties

In some embodiments, the nanoparticles do not require a targeting moiety, and effectively reach their intended cells or tissues in the absence of a targeting moiety. In other embodiments, the nanoparticles contain a targeting moiety conjugated to the surface of the nanoparticle that binds a component of a cell. In some embodiments, the targeting moiety is covalently linked to the nanoparticle. In other embodiments, the targeting moiety is non-covalently linked to the nanoparticle. A targeting moiety may be a peptide, polypeptide, glycoprotein, nucleic acid, small molecule, carbohydrate, lipid, etc. that binds to one or more targets associated with an organ, tissue, cell, or extracellular matrix. In some embodiments, the targeting moiety increases or enhances targeting of the nanocarrier to a desired cell type or tissue.

B. Hyperosmolar Solutions

The nanoparticles are administered with a hyperosmolar solution. In a preferred embodiment, the hyperosmolar solution is a saline or mannitol solution. The concentrations of the hyperosmolar solutions range from between 0.1% and 10%. In some embodiments, the concentrations of the hyperosmolar solutions are 0.9%, 3% and 9%. In a preferred embodiment, the hyperosmolar solution is saline. In a more preferred embodiment, the concentration of the hyperosmolar saline solution is 3%.

C. Pharmaceutical Excipients for Delivery to the Brain

The particles may be administered in combination with a physiologically or pharmaceutically acceptable carrier, excipient, or stabilizer. Pharmaceutical compositions may be formulated in a conventional manner using one or more physiologically acceptable carriers including excipients and auxiliaries which facilitate processing of the active compounds into preparations which can be used pharmaceutically.

The nanoparticles may be protected initially by the addition of pharmaceutical excipients and then increasing the osmolarity of the solution by adding NaCl immediately prior to CED administration. In the preferred embodiment, the pharmaceutical excipient is exposed to the hyperosmolar saline for as short a time as possible to avoid any adverse effects.

Proper formulation is dependent upon the route of administration chosen. In preferred embodiments, the particles are formulated for parenteral delivery to the brain. Typically the particles will be formulated in sterile saline or buffered solution for injection into the tissues or cells to be treated. The particles can be stored lyophilized in single use vials for rehydration immediately before use. Other means for rehydration and administration are known to those skilled in the art.

Optional pharmaceutically acceptable excipients include, but are not limited to, lubricants, disintegrants, colorants, stabilizers, and surfactants. Stabilizers are used to inhibit or retard decomposition reactions which include, by way of example, oxidative reactions.

The nanoparticles or nanoconjugates can be formulated in dosage unit form for ease of administration and uniformity of dosage. The expression "dosage unit form" as used herein refers to a physically discrete unit of conjugate appropriate for the patient to be treated. It will be understood, however, that the total daily usage of the compositions will be decided by the attending physician within the scope of sound medical judgment. For any nanoparticle or nanoconjugate, the therapeutically effective dose can be estimated initially either in cell culture assays or in animal models, usually mice, rabbits, dogs, or pigs. The animal model is also used to achieve a desirable concentration range and route of administration. Such information can then be used to determine useful doses and routes for administration in humans. Therapeutic efficacy and toxicity of conjugates can be determined by standard pharmaceutical procedures in cell cultures or experimental animals, e.g., ED50 (the dose is therapeutically effective in 50% of the population) and LD50 (the dose is lethal to 50% of the population). The dose ratio of toxic to therapeutic effects is the therapeutic index and it can be expressed as the ratio, LD50/ED50. Pharmaceutical compositions which exhibit large therapeutic indices are preferred. The data obtained from cell culture assays and animal studies can be used in formulating a range of dosages for human use.

II. Methods of Manufacture

A. Nanoparticles

The polymers will typically be obtained commercially or can be synthesized by any means known in the art. PEG or other coating agents can be conjugated to the core polymer using a variety of techniques known in the art depending on whether the coating is covalently or non-covalently associated with the particles. In some embodiments the PEG or other coating agent can be covalently attached to the core polymer by reacting functional groups on the particles with reactive functional groups on the PEG or other coating agent to make a copolymer. For example, aminated PEG can be reacted with reactive functional groups on the particles, such as carboxylic acid groups, to covalently attach the agent via an amide bond.

In one embodiment, methoxy-PEG (5 kDa)-amine is conjugated to the carboxyl function group on the surface of carboxylated polymeric nanoparticles. In other embodiments, the nanoparticles are formed from a PLGA-PEG co-polymer with PEG constituting 25 wt % of the co-polymer.

In some embodiments nanoparticles are formed of a mixture of PEGylated and non-PEGylated polymers. The molar ratio of the PEGylated:non-PEGylated polymers can be varied to alter the density of the surface displayed PEG.

The nanoparticles can be formed from one or more biocompatible polymer, biodegradable polymer, or both, one or more PEGs or other coating agents, using any suitable method for the formation of polymeric nanoparticles known in the art. The methods employed for nanoparticle formation will depend on a variety of factors, including the characteristics of the polymers present in the nanoparticles, as well as the desired particle size and size distribution.

In circumstances where a monodisperse population of particles is desired, the particles may be formed using a method which produces a monodisperse population of nanoparticles. Alternatively, methods producing polydisperse nanoparticle distributions can be used, and the particles can be separated using methods known in the art, such as sieving, following particle formation to provide a population of particles having the desired average particle size and particle size distribution.

Common techniques for preparing nanoparticles include, but are not limited to, solvent evaporation, solvent removal, spray drying, phase inversion, low temperature casting, and nanoprecipitation. Suitable methods of particle formulation are briefly described below. Pharmaceutically acceptable excipients, including pH modifying agents, disintegrants, preservatives, and antioxidants, can optionally be incorporated into the particles during particle formation. As described above, one or more additional active agents can also be incorporated into the nanoparticle gene carrier during particle formation.

1. Solvent Evaporation

In this method the polymer is dissolved in a volatile organic solvent, such as methylene chloride. Nucleic acid is added to the solution, and the mixture is suspended in an aqueous solution that contains a surface active agent such as poly(vinyl alcohol). The resulting emulsion is stirred until most of the organic solvent evaporated, leaving solid nanoparticles. The resulting nanoparticles are washed with water and dried overnight in a lyophilizer. Nanoparticles with different sizes and morphologies can be obtained by this method. This method is useful for relatively stable polymers like polyesters and polystyrene.

However, labile polymers, such as polyanhydrides, may degrade during the fabrication process due to the presence of water. For these polymers, the following two methods, which are performed in completely anhydrous organic solvents, are more useful.

2. Solvent Removal

This technique is primarily designed for polyanhydrides. In this method, the drug is dispersed or dissolved in a solution of the selected polymer in a volatile organic solvent like methylene chloride. This mixture is suspended by stirring in an organic oil (such as silicon oil) to form an emulsion. Unlike solvent evaporation, this method can be used to make nanoparticles from polymers with high melting points and different molecular weights. The external morphology of spheres produced with this technique is highly dependent on the type of polymer used.

3. Spray-Drying

In this method, the polymer is dissolved in organic solvent. A known amount of the active drug is suspended (insoluble drugs) or co-dissolved (soluble drugs) in the polymer solution. The solution or the dispersion is then spray-dried.

4. Phase Inversion

Microspheres can be formed from polymers using a phase inversion method wherein a polymer is dissolved in a "good" solvent, fine particles of a substance to be incorporated, such as a drug, are mixed or dissolved in the polymer solution, and the mixture is poured into a strong non solvent for the polymer, to spontaneously produce, under favorable conditions, polymeric microspheres, wherein the polymer is either coated with the particles or the particles are dispersed in the polymer. The method can be used to produce nanoparticles in a wide range of sizes, including, for example, about 100 nanometers to about 10 microns. Exemplary polymers which can be used include polyvinylphenol and polylactic acid. Substances which can be incorporated include, for example, imaging agents such as fluorescent dyes, or biologically active molecules such as proteins or nucleic acids. In the process, the polymer is dissolved in an organic solvent and then contacted with a non-solvent, which causes phase inversion of the dissolved polymer to form small spherical particles, with a narrow size distribution optionally incorporating an antigen or other substance.

Other methods known in the art that can be used to prepare nanoparticles include, but are not limited to, polyelectrolyte condensation (see Suk et al., *Biomaterials,* 27, 5143-5150 (2006)); single and double emulsion (probe sonication); nanoparticle molding, and electrostatic self-assembly (e.g., polyethylene imine-DNA or liposomes).

III. Methods of Use

It has been established that the density and composition of a surface coating agent such as PEG can determine the ability of the particles to diffuse throughout the brain parenchyma. The diffusion limitations of nanoparticles (~50-75 nm diameter particles) was investigated ex vivo, in excised rodent brain slices, as described in the Examples. Using multiple particle tracking (MPT) and optimized PEGylation protocols, it was shown that PEG coating and differences in the concentrations of infusion solutions prevent the shielding particles from adhesive interactions and increase their diffusivity, enabling them to penetrate and distribute more extensively in vivo, compared to a reference particle without PEG or other coating agent.

Therefore, the particle compositions described herein can be used to administer one or more therapeutic, prophylactic, and/or diagnostic agents directly to the brain to treat one or more diseases or disorders of the brain.

A. Therapeutic Uses

Nanoparticles carrying one or more therapeutic, diagnostic or prophylactic agents can be utilized to deliver these agents for therapeutic, diagnostic or prophylactic purposes, such as in a method for delivering chemotherapeutics.

1. Disorders or Diseases to be Treated

Exemplary diseases and disorders of the brain that can be treated by the disclosed compositions and methods include neoplasms (cancers, tumors, growths), infections (HIV/AIDS, Tuberculosis), inflammation (multiple sclerosis, transverse myelitis and other autoimmune processes, cerebral or tissue edema and other reactive processes), acquired or degenerative conditions (Alzheimer's disease, Parkinson's disease, stroke, amyotrophic lateral sclerosis, acute and chronic traumatic and pain syndromes), congenital or genetic abnormalities (neurofibromatosis, mucopolysaccaridoses, tuberous sclerosis, Von Hippel Lindau), epigenetic conditions and brain trauma or injury.

B. Methods of Administration and Dosing

The disclosed nanoparticles can be administered by a variety of routes of administration. In certain embodiments the particles are administered directly to the brain. In other embodiments the particles are administered systemically.

The composition of the brain ECM, including the physico-chemical properties of its components and the space between them ('pores'), are key factors that determine the penetration of substances within the brain.

Unshielded, negatively charged particles with exposed hydrophobic regions have significantly hindered diffusion regardless of particle size. The hydrophobic interactions between particle surfaces and ECM components can be a source of significant adhesion. Adequate surface shielding from potential interactions, including electrostatic and hydrophobic forces, are crucial for rapid diffusion in the brain.

Mechanisms for the enhanced delivery of the disclosed nanoparticles to the brain are disclosed. Enhanced local delivery can be achieved via convection, electricomagnetic, or other forces. Enhanced systemic delivery can be achieved via co- or sequential administration with permeabliization agents such as but not limited to pharmacologic substances (e.g. cytokines), mechanical barrier disruption (e.g. ultrasound), or osmotic changes (e.g. mannitol). Other methods of delivery include intrathecal or intra-ventricular delivery via cerebro-spinal fluid spaces, intra-nasal administration or delivery via the olfactory bulb and systemic delivery via oral, intravenous, or intra-arterial administration.

1. Convection Enhanced Delivery

In some embodiments PEGylated NPs are provided in a hyperosmolar solution to enhance the distribution of the NPs within the ICS of the brain, following convection enhanced delivery (CED). CED is a method in which drugs are delivered through a needle installed intraparenchymally into the brain and attached to a pump providing positive pressure and constant flow of the infusates. For example, densely PEGylated nanoparticles containing therapeutic or diagnostic agents on the surface, encapsulated within the nanoparticle, or both can be delivered in a hyperosmolar solution through one to several catheters placed stereotactically, for example, directly within a brain tumor mass or around the tumor or the resection cavity.

In some embodiments the hyperosmolar solution and PEGylation significantly enhances distribution of varied-size NPs' locoregional concentration. In certain embodiments the use of CED to deliver densely PEGylated particles in a hyperosmolar solution enhances the distribution of the particles throughout the brain to an extent that is greater than expected. In some embodiments NP distribution is achieved throughout the entire striatum. CED alone is unlikely to provide a significant benefit if particles, such as the reference particles, remain localized at sites of infusion or in the brain PVS due to any of adhesive interactions, steric obstruction and preferential trafficking and sequestration. Thus, physicochemical properties of particles that allow unhindered diffusion in the brain parenchyma remain critical for achieving enhanced particle penetration following the CED.

2. Administration Regimes

In general the timing and frequency of administration will be adjusted to balance the efficacy of a given treatment or diagnostic schedule with the side-effects of the given delivery system. Exemplary dosing frequencies include continuous infusion, single and multiple administrations such as hourly, daily, weekly, monthly or yearly dosing.

Regardless of systemic, intrathecal, or local delivery into the brain parenchyma itself, penetration of bioactive or imaging agents in the brain and other tissues has been a key hurdle to effective therapy and diagnostics. Numerous studies using viral, nanoparticle, and convection-enhanced delivery have failed due to limited movement of substances within the brain. Therefore, defining the critical limiting parameters and designing strategies to enhance brain penetration will likely improve the efficacy of these treatments. Densely-PEGylated nanoparticles offer numerous additional advantages, including increased particle diffusion, improved stability, and prolonged sustained-release kinetics. These factors are known to correlate with the efficacy of many therapeutics and will likely have a significant impact on the utility of nano-sized carriers for diagnostic and therapeutic delivery to the brain.

EXAMPLES

The present invention will be further understood by reference to the following non-limiting examples.

Example 1: Effects of Coating Particles with Non-adhesive Coating

Materials and Methods i. Nanoparticle Preparation and Characterization 40-nm dark red fluorescent carboxylated polystyrene microspheres (PS-COOH) (Life Technologies, Grand Island, N.Y.) were modified by conjugating a dense layer of 5 kDa methoxy-PEG-amine (Creative PEGworks, Winston Salem, N.C.), onto the surface, according to a previously published protocol (Nance, E. A., et al., Sci Transl Med, 2012, 4(149), 149ra119), to obtain densely PEGylated polystyrene nanoparticles (PS-PEG). PLGA (75:25) (MW: 15 kDa; Jinan Daigang Biomaterials Co. Ltd., Jinan, China) and PLGA-PEG (75:25) (25 wt % PEG; Jinan Daigang Biomaterials Co. Ltd., Jinan, China) nanoparticles were formulated using the single emulsion process according to a previously published protocol (Nance, E., et al., ACS Nano, 2014, 8(10), 10655-10664). Briefly, PLGA-PEG and PLGA polymer were fluorescently labeled with AlexFluor 647 and AlexaFluor 555 cadaverine dye (Molecular Probes, Eugene, Oreg.) respectively as described by Nance, E., et al., ACS Nano, 2014, 8(10), 10655-10664. Polymers were dissolved in dichloromethane and emulsified using a probe sonicator in 0.5 wt % cholic acid (Sigma Aldrich, St. Louis, Mo.). Nanoparticles were filtered through a 1 μm filter (Whatman, GE Healthcare, Pittsburgh, Pa.). PLGA-PEG were collected and washed using centrifugal filter units (MWCO: 100 kDa, Millipore, Billerica, Mass.) at a speed of 3600 g for 12 min. PLGA nanoparticles were collected by high speed centrifuge at 22170 g for 30 min, washed, and resuspended for use. A small aliquot was lyophilized and weighed to determine concentration of collected nanoparticles. Nanoparticle size and surface chemistry were characterized in a standard 10 mM NaCl solution through dynamic light scattering and laser doppler anemometry techniques using a Zetasizer NanoZS (Malvern Instruments, Southborough, Mass.). To test nanoparticle stability, the particles were diluted 200-fold in the following infusate solutions: water, saline (0.9%, 3%) and mannitol (10%, 25%) and allowed to incubate for 15 minutes at room temperature. Nanoparticles were then sized again using dynamic light scattering to determine hydrodynamic diameters using a Zetasizer NanoZS. When preparing nanoparticles for intracranial convection enhanced delivery (CED), stock PS-PEG and PS-COOH were each diluted 25-fold in water, 0.9% saline, 3% saline, 10% mannitol, or 25% mannitol and mixed at a 1:1 ratio for a final concentration of 1 mg/mL. Additional nanoparticle concentrations were also investigated including final concentrations of 25 mg/mL and 0.1 mg/mL in normal saline. For PLGA and PLGA-PEG, nanoparticles were lyophilized overnight and resuspended at a concentration of 1 mg/mL in 0.9% saline for administration.

ii. Convection Enhanced Delivery

Female CF-1 mice weighing 20-30 g in mass or male Sprague Dawley rats weighing 300-400 g in mass were anesthetized with a mixture of ketamine (75 mg/kg) and xylazine (7.5 mg/kg). For mice, a 2 cm sagittal incision was made on the head and a burr hole was made 2 mm lateral to the bregma. All nanoparticle solutions or infusate solutions were loaded into a 504 Hamilton Neurosyringe with a 33 gauge syringe and set with a 1 mm step (Hamilton, Reno, Nev.). The syringe was vertically mounted on a Chemyx Nanojet Injector Module (Chemyx, Stafford, Tex.) which was held on a small animal stereotactic frame (Stoelting, Wood Dale, Ill.). The loaded syringe was lowered to a depth of 2.5 mm below the mouse dura and a total of 2 μL of the solution was administered over 10 minutes at a rate of 0.2 μL/min. For rats, a burr hole was made 3 mm lateral to the bregma and a total solution of 204 of solution was administered at a depth of 3.5 mm at a rate of 0.334/min. In both rodents, the cannula was allowed to sit for 5 minutes following the completion of infusion and was then withdrawn at a rate of 1 mm/min. The animal was then sutured (Covidien, Mundelein, Ill.) and placed on a heating pad.

iii. Different Nanoparticle Concentrations: Volume of Distribution Quantification When investigating the volume of distributions for varying PS-PEG and PS-COOH concentrations, fluorescent brain slice images were taken above the background as determined in the contralateral hemisphere. Brain slice images were stacked using Metamorph (Metamorph, Sunnyvale, Calif.) and then aligned using the StackReg plugin (ImageJ, NIH, Bethesda, Md.). A 3D rendering of the nanoparticle volume of distribution was generated using Imaris (Bitplane, South Windsor, Conn.) software employing a threshold of 10% of the maximum fluorescent intensity. This quantification method was taken to ensure that the nanoparticle Vd at the lowest infusion concentration was fully captured.

iv. Blood Vessel Staining and Imaging

Mice were co-injected with fluorescent dark red PS-PEG and red PS-COOH nanoparticles. Tissues were harvested, post-fixed, and cryosliced at 10 μm thickness at designated intervals from the coronal plane of injection (0 mm, 0.5 mm, 1.0 mm, and 1.5 mm). Tissues were mounted on glass slides and immersed in pepsin solution (Dako, Carpinteria, Calif.) at 37° C. for 10 minutes. Slides were washed 3 times with PBS and blocked with blocking buffer composed of 5% normal goat serum (Sigma Aldrich, St. Louis, Mo.) and 1% bovine serum albumin (Sigma Aldrich, St. Louis, Mo.) in PBS for 1 hour at room temperature. Tissue slices were incubated with primary rabbit anti-mouse collagen IV antibody (Abcam ab6586, Cambridge, Mass.) diluted 1:250 in blocking buffer for 16 hours at 4° C. Tissues were washed 3 times with PBS and incubated with a AF488 labeled goat anti-rabbit secondary antibody (Life Technologies, Grand Island, N.Y.) diluted 1:500 in blocking buffer for 1 hour at room temperature. Tissues were washed 3 times with PBS, and then incubated with DAPI (Life Technologies, Grand Island, N.Y.) at a 1:1000 dilution in PBS for 15 minutes at room temperature. Slides were washed 3 times with PBS and allowed to dry before mounting with Dako fluorescence mounting medium (Dako, Carpinteria, Calif.).

Using a Zeiss confocal 710 laser scanning microscope, high resolution images (40× magnification) were taken at the designated intervals away from the main NP bulk and imaged for DAPI, collagen IV, PS-PEG, and PS-COOH. Images were derived from N=3 mice specimen with at least N=3 images per animal. Presence of fluorescent PS-PEG and PS-COOH in PVS and ICS were qualitatively determined in all images. Presence of NP in extracellular space (ECS) and ICS were categorized into the following groups: 1) consistent in 100% of images, 2) consistent in 90% of all images, 3) consistent in 80% of all images, and 4) consistent in less than 20% of all images.

v. Lateral Striate Artery Distribution of Nanoparticles

The lateral striate arteries in the rodent striatum were visually identified in the imaged slices by identifying elongated and flattened endothelial cells following a DAPI stain (Life Technologies, Grand Island, N.Y.). Co-staining these endothelial cells with blood vessel basement membrane (Collagen IV) confirmed their lining of the striate artery. High resolution images using a Zeiss confocal 710 laser scanning microscope (40× magnification) were taken of PS-PEG and PS-COOH in the striate artery. To determine the extent of nanoparticle escape from PVS, images were processed through a custom MATLAB script. A line was drawn parallel along DAPI-stained endothelial cells that defined the striate artery. Fluorescent nanoparticles intensities were averaged at 10 μm intervals up to 100 μm away from the striate artery. At least N=3 striate artery vessels were quantified in each condition. The percent NP coverage within the parenchymal ICS on each high resolution image (40× magnification) was calculated by using the custom MATLAB quantification script which thresholded the images at 10% of the maximum intensity. Flattened, DAPI-stained endothelial cells that line the striate artery were used to delineate the PVS and the ICS and only detectable fluorescence throughout the ICS was quantified. At least N=3 striate artery images were quantified for each condition.

Results

Shielding Nanoparticle Surface Charge Enhances Nanoparticle Distribution

Fluorescently labeled 40-nm carboxylated polystyrene (PS-COOH) NP probes were modified with exceptionally dense surface PEG coatings according to our previously published protocol (Nance, E. A., Sci Transl Med, 2012 4(149), 149ra119). These densely PEGylated NPs (PS-PEG) were approximately 60 nm with a near neutral surface charge (as indicated by ζ-potential), whereas unmodified, PS-COOH possessed a significantly anionic surface charge (FIG. 1A).

Figure 1B:
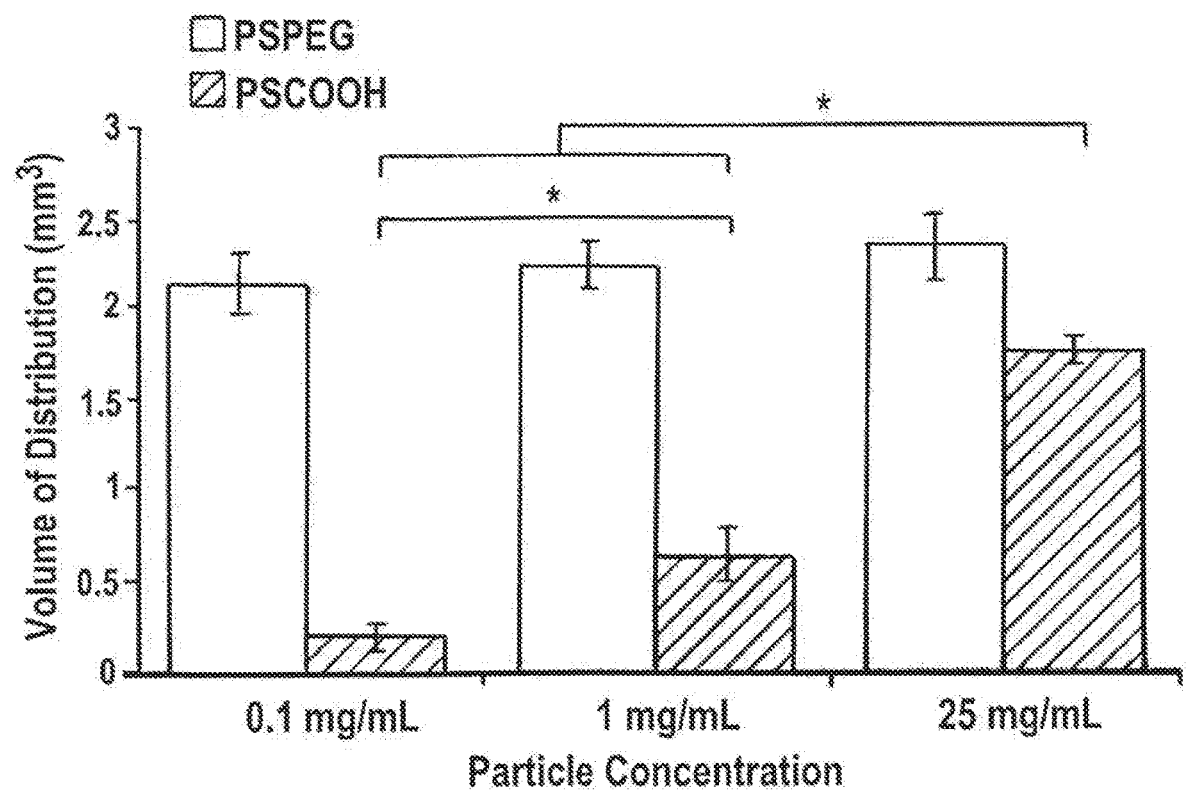
Figure 1C:
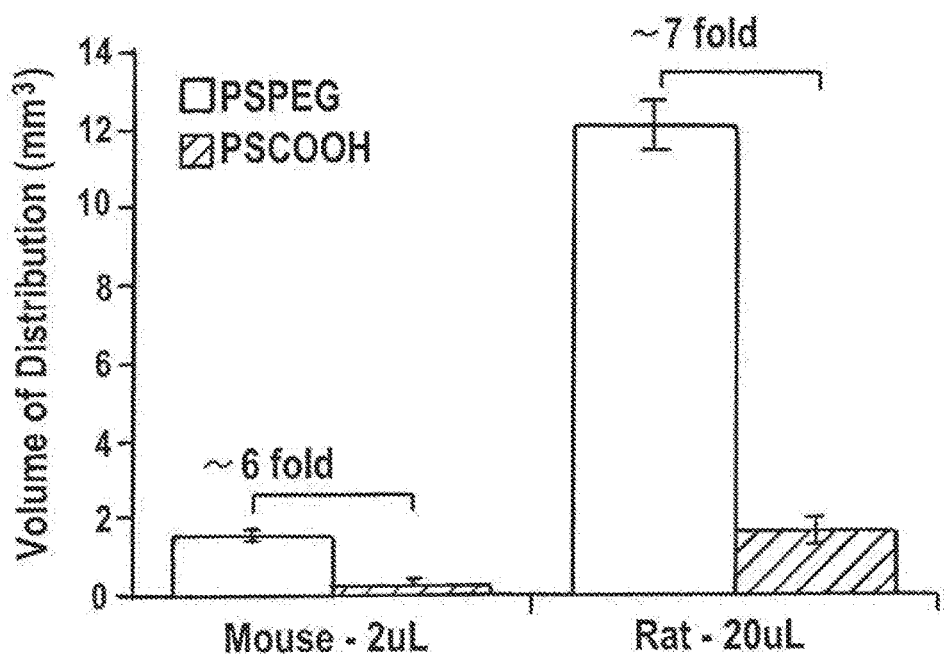
FIG. 1C is a graph of nanoparticle volume of distributions in CF-1 mouse and Sprague Dawley rats following in vivo administration of PS-PEG and PS-COOH.

Previous studies that have used CED to administer sub-100 nm, non-shielded NP fail to achieve significant NP distribution, likely due to adhesive interactions between the NP and the brain ECM (Saito, et al., J Neurosci Methods, 2006, 154(1-2), 225-32). NP as large as 114 nm with exceptionally dense PEG coatings can rapidly diffuse in healthy and tumor rodent brain tissues, thereby leading to improved therapeutic outcome (Nance, et al., Sci Transl Med, 2012, 4(149), 149ra119; Nance, et al., ACS Nano, 2014, 8(10), 10655-10664). This study shows that the pressure-driven flow provided by CED further improves the distribution of non-adhesive NP throughout the brain interstitium in both CF-1 mice and Sprague Dawley rats (FIG. 1C). Following infusion at a NP concentration of 1 mg/mL, the volume of distribution (Vd) of non-adhesive NP was consistently higher (~6-7 fold) than that of unmodified PS-COOH in both species. It was concluded that even the continuous pressure-driven flow provided by CED cannot adequately overcome the adhesive interactions that occur between conventional NP (i.e., PS-COOH) and the brain ECM. Thus, a well-coated, non-adhesive nanoparticle surface is essential to achieving significant distribution of NP away from the point of administration following CED.

In an attempt to address the limited NP distribution, several groups have administered high concentrations of small, conventional NP that saturate the available binding domains throughout the ECM, thereby enabling residual NP to distribute away from the point of infusion (MacKay, et al., Brain Res, 2005, 1035(2), 139-53; Zhou, et al., Proc Natl Acad Sci U.S.A., 2013 110(29), 11751-56; Kroll, et al., Neurosurgery, 1996, 38(4), 746-52; discussion 752-4). Therefore, the correlation between Vd of NP and infused NP concentration was determined. When PS-PEG and PS-COOH were co-infused at 0.1 mg/mL, 1 mg/mL, and 25 mg/mL, Vd of PS-PEG was 10.7-fold, 3.6-fold, and 1.3-fold higher than that of PS-COOH, respectively (FIG. 1B). Importantly, the Vd of PS-COOH was highly correlated with the infused NP concentration whereas PS-PEG achieved high Vd independent of concentration (FIG. 1B).

The data establish that non-adhesive NP can overcome the brain ECM and achieve significant distributions within the brain interstitium, even when administered at low concentrations. Conventional NP overcome the brain ECM following CED only if they are administered at extremely high NP concentrations (FIG. 1B), which may not be translationally applicable for highly immunogenic and/or toxic drug payloads.

Example 2: Effects of Different Concentrations of Infusate Composition

Materials and Methods
i. Ex Vivo Characterization of Brain Pore Sizes

Brains from female CF-1 mice were harvested and multiple particle tracking was conducted on nanoparticles injected into 1.5 mm thick brain slices according to a slightly modified protocol of Nance, et al., Sci Transl Med, 2012, 4(149), 149ra119. Briefly, the harvested rodent brain was rinsed in chilled artificial spinal fluid and sliced at 1.5 mm intervals using a Zivic mouse brain mold (Zivic Instruments, Pittsburgh, Pa.). Individual brain slices were immersed in infusate solutions (water, 0.9% saline, 3% saline, 10% mannitol, or 25% mannitol) for 5 minutes. Brain slices were removed and mounted on a custom made well and 0.5 μL of fluorescently labeled PS-PEG nanoparticles were injected into the cortex. A coverslip was glued on top of the specimen to prevent bulk flow in the tissue. The particle trajectories were recorded as 20 second movies at an exposure of 66 ms using an EMCCD camera (Evolve 512; Photometrics, Tucson, Ariz.) mounted on an inverted epifluorescence microscope (Axio Observer D1, Zeiss; Thornwood, N.Y.) equipped with a 100× oil-immersion objective (N.A., 1.3). Nanoparticle mean squared displacements (MSD) were calculated based on a custom MATLAB nanoparticle tracking code and histograms of particle MSD.

ii. Nanoparticle Volume of Distribution Quantification

Animals were sacrificed 1 hour post-CED and the brains were fixed in formalin for 24 hours and subsequently exposed to a 10%, 20%, and 30% sucrose gradient. Brains were mounted and cryosectioned at a thickness of 50 μm (Leica Biosystems, Buffalo Grove, Ill.). Distances ±1.5 mm from the injection site were carefully obtained. Slices were fixed with Dako fluorescence mounting medium (Dako, Carpinteria, Calif.) and imaged using a Zeiss confocal 710 laser scanning microscope (Zeiss, Jena, Germany) in the GFP and Cy5 channels at 5× magnification. The presence of background fluorescence was determined by comparing to the striatum of the contralateral hemisphere with no injection. Brain slice images were quantified for fluorescent distribution of PS-PEG or PS-COOH nanoparticles by running the confocal laser scanning microscope images through a custom MATLAB script which thresholded the images at 10% of the maximum intensity. Fluorescent distribution of NP in the ventricles or white matter tracts were avoided and not included in the quantification. The area of distribution calculated from each slice was multiplied by the slice thickness of 50 μm and summated across all images to obtain a total volume of distribution. If a slice was lost during cryosection procedure, the area of distribution was taken as the average of the previous and following slices. Rarely was more than 1 slice lost from a brain specimen. Furthermore, to ensure that the observed Vd differences between the PS-COOH and PS-PEG nanoparticles was not due to the use of GFP and Cy5 channels, the fluorescent markers switched to confirm that fluorescent PS-PEG nanoparticles (Yellow-green, GFP) exhibited significantly enhanced distribution as compared to PS-COOH nanoparticles (Dark-red, Cy5).

iii. Toxicity of Different Infusate Solutions

Following intracranial administration of the various infusate solutions (no NP), CF-1 mice were monitored for adverse signs of toxicity. Mice were sacrificed either 1 hour or 72 hours post-administration. Brains were harvested and fixed in formalin for 24 hours followed by H&E staining analysis conducted by the Johns Hopkins Reference Histology. The injection point was identified by the tissue cavity imparted by the needle and the region immediately adjacent was imaged and evaluated for evidence of toxicity or hemorrhage by a board certified neuropathologist.

Statistical testing between two groups was conducted using a two sample student t-test. If statistical comparisons involved more than two groups, testing was conducted with SPSS 18.0 software (IBM Inc.) using one-way ANOVA followed by Tukey honestly significant difference. Differences for t-test, ANOVA, and Tukey tests were considered statistically significant at $p<0.05$.

Results
i. Enlarging Brain Extracellular Space Enhances Nanoparticle Distribution For non-adhesive NPs that are shielded from adhesive interactions with the brain ECM, the steric obstruction imposed by the ECM components constitutes the main limitation to efficient NP distribution (Nance, et al., Sci Transl Med, 2012, 4(149), 149ra119; Sykova and Nicholson, Physiol Rev, 2008, 88(4), 1277-340). To overcome this barrier, prior studies have modulated the brain tissue to enlarge the pore sizes of the brain ECM and enhance therapeutic distribution (Neeves, et al., Brain Res, 2007, 1180, 121-32; Chen and Nicholson, Proc Natl Acad Sci U.S.A, 2000, 97(15), 8306-11; Mastakov, et al., Mol Ther, 2001, 3(2), 225-32; Mamot, et al., J Neurooncol, 2004. 68(1), 1-9). Nicholson and coworkers demonstrated that exposure of brain tissues to modestly hyperosmolal solutions (500 mOsmol/kg) increases the volume of ICS and minimizes the tissue's cumulative resistance to NP diffusion (Kume-Kick, et al., J Physiol, 2002. 542(Pt 2), 515-27). Here, the pore sizes of the brain ECM were altered by administering well-shielded NP in infusate solutions of varying osmolarities. Hyperosmolar saline and mannitol solutions were used since they have both been administered in clinical settings for reducing elevated intracranial pressure (Kamel, et al., Crit Care Med, 2011, 39(3), 554-9). Furthermore, mannitol has been extensively investigated as a hyperosmolar infusate solution for CED of therapeutics in preclinical studies (Neeves, et al., Brain Res, 2007, 1180, 121-32; Mamot, et al., J Neurooncol, 2004, 68(1), 1-9; Carty, et al., J Neurosci Methods, 2010, 194(1), 144-53). All infusate solutions were deemed safe following histological analysis of H&E stained mouse brains by a board-certified neuropathologist.

To determine the changes in ECM pore sizes following exposure of the brain microenvironment to solutions of different osmolarities, pore sizes of the brain were probed using an established ex vivo technique (Nance, et al., Sci Transl Med, 2012, 4(149), 149ra119; Nance, et al., J Control Release, 2014, 189, 123-32). The PS-PEG physicochemical characteristics were unaffected in the infusate solutions (Table 1), thereby insuring the effect of osmolarity on ECM pore size was accurately assessed.

TABLE 1

Sizes of PS-PEG and PS-COOH NP in hypo-osmolar, iso-osmolar or hyperosmolar saline solutions.

| Infusate solution | Water | 0.9% saline | 3% saline |
|---|---|---|---|
| Osmolarity (mOsm/L) | 0 | ~300 | ~1000 |
| Viscosity | 0.89 | 0.90 | 0.94 |
| PS-PEG (nm) | 58 ± 0.2 | 61 ± 2 | 62 ± 0.5 |
| PS-COOH (nm) | 51 ± 1 | 45 ± 2 | 1330 ± 370 |

Figure 2A:
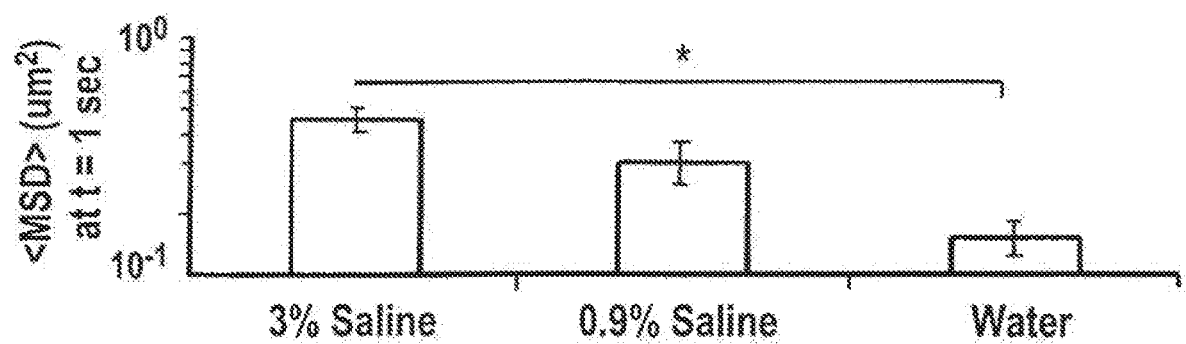
FIGS. 2A and 2B are graphs characterizing nanoparticle diffusivity ex vivo and distribution in vivo.

The brain slices were incubated in hypo-osmolar water, iso-osmolar 0.9% saline, or hyperosmolar 3% saline and multiple particle tracking (MPT) used to quantify the diffusion of non-adhesive PS-PEG probes (Nance, et al., Sci Transl Med, 2012, 4(149), 149ra119). At a timescale of 1 second, brain slices treated with hyperosmolar 3% saline yielded 1.5-fold higher NP mean squared displacements (MSD) compared to brain slices incubated in normal saline (FIG. 2A). This indicates that water drawn into ICS via the osmotic gradient generated by hyperosmolar saline enlarged the ECM mesh spacing (Chen and Nicholson, Proc Natl Acad Sci U.S.A, 2000, 97(15), 8306-11; Kume-Kick, et al., J Physiol, 2002. 542(Pt 2), 515-27), thereby reducing the steric hindrances imposed on PS-PEG traveling within the brain ICS. On the contrary, brain slice treatment with hypo-osmolar water solution yielded 2-fold lower MSD values (FIG. 2A). This reduced PS-PEG diffusivity is due to an increase in steric hindrances resulting from the engorging of cellular structures driven by water intake and subsequent reduction of ICS (Chen and Nicholson, Proc Natl Acad Sci U.S.A, 2000, 97(15), 8306-11).

Figure 2B:
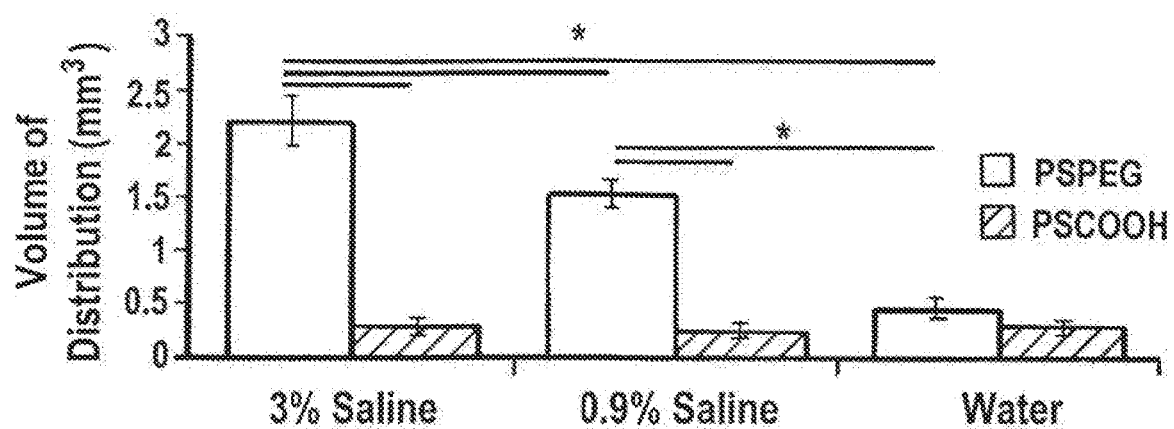

To verify that the osmotic modulation of ICS observed ex vivo translates in vivo, NP were administered using CED in saline infusate solutions with varying osmolarities and their effect on the Vd of NP determined. Results demonstrated that the Vd of non-adhesive PS-PEG was positively correlated with the osmolarity of the infusate solution. However, higher osmolarity solutions did not significantly affect the Vd of PS-COOH (FIG. 2B). This indicates that even when steric hindrances were minimized, adhesive interactions remained a dominating limitation for conventional NP. In fact, when infused in iso-osmolar and hyperosmolar solutions, Vd of PS-PEG was 5.8-fold and 6.8-fold higher than that of PS-COOH, respectively. In contrast, the Vd of PS-PEG and PS-COOH were not significantly different when hypo-osmolar water was used as an infusate solution, suggesting that the elevated steric hindrances stemming from a reduction in ECM pore sizes serve as the dominant limitation to NP distribution. These observations emphasize the importance of simultaneously minimizing adhesive interactions and steric hindrances in order to maximize NP distribution in the brain interstitium following CED.

CED of a non-adhesive NP in a hyperosmolar infusate solution is valid only if the NP physicochemical characteristics are retained. It was found that increasing the osmolarity of mannitol infusate solutions (from 10% to 25%) significantly reduced PS-PEG diffusivity in brain tissues ex vivo and distribution in vivo. Since the osmolarity is a colligative property independent of solute type, the contrary findings are not likely due to any unique effect mannitol-based osmotic driven water flow. Rather, the results can be attributed to the marked increase in the size of PS-PEG in 25% mannitol infusate solution, which offset the effect of enlarged ECM pores (Table 2).

TABLE 2

Sizes of PS-PEG and PS-COOH NP in 10% and 25% mannitol solutions.

| Infusate solution | 10% mannitol | 25% mannitol |
|---|---|---|
| Osmolarity (mOsm/L) | ~500 | ~1250 |
| Viscosity | 1.22 | 2.14 |
| PS-COOH (nm) | 64 ± 1 | 86 ± 3 |
| PS-PEG (nm) | 79 ± 2 | 121 ± 9 |

PVS, also known as Virchow Robin spaces in the brain, serve as a conduit for rapid flow of CSF into the brain from the subarachnoid space (Pardridge, Fluids Barriers CNS, 2011, 8(1), 7) and are responsible for the clearance of small metabolic molecules and waste products (Iliff, et al., Sci Transl Med, 2012, 4(147), 147ra111). Numerous studies have demonstrated that the distribution of therapeutics at large distances away from the injection site takes place predominantly through the PVS (Krauze, et al., Exp Neurol, 2005, 196(1), 104-11; Barua, et al., Fluids Barriers CNS, 2012, 9(1), 2). However, preferential trafficking and subsequent sequestration of intracranially administered NP in PVS (Carare, et al., Neuropathol Appl Neurobiol, 2008, 34(2), 131-44) significantly reduce the available NP dose for treating target cells. Excessive therapeutic buildup within PVS has also resulted in toxic side effects to neighboring macrophages (MacKay, et al., Brain Res, 2005, 1035(2), 139-53), undesired immune responses (Barua, et al., Fluids Barriers CNS, 2012, 9(1), 2), and an overall reduction in therapeutic efficacy (Krauze, et al., Exp Neurol, 2005, 196(1), 104-11; Barua, et al., Fluids Barriers CNS, 2012, 9(1), 2).

It was hypothesize that the fraction of NP that distribute through the ICS as opposed to the PVS would be increased by modulating the brain tissue to reduce the resistance of the brain ECM to NP diffusion. A study was therefore conducted to investigate the extent of NP trafficking within PVS when infused in water, 0.9%, and 3% saline. PS-PEG NPs administered in water were largely confined in the PVS (Table 3).

TABLE 3

High resolution images from N = 3 mice (Total of N ≥ 10 images) were analyzed for presence of PS-COOH and PS-PEG in PVS and ICS at specific distances from the plane of administration.*

| | | PS-COOH | | | | PS-PEG | | | |
|---|---|---|---|---|---|---|---|---|---|
| | | 0 mm | 0.5 mm | 1.0 mm | 1.5 mm | 0 mm | 0.5 mm | 1.0 mm | 1.5 mm |
| PVS | Water | ++ | ++ | ++ | ++ | ++ | ++ | ++ | ++ |
| | 0.9% saline | ++ | ++ | * | | ++ | ++ | ++ | ++ |
| | 3% saline | + | * | | | ++ | ++ | ++ | ++ |
| ICS | Water | | | | | * | | | |
| | 0.9% saline | | | | | | ++ | ++ | ++ |
| | 3% saline | | | | | | ++ | ++ | ++ |

Boxes with "++" indicate that 90-100% of images depict the presence of NP.
Boxes with "+" indicate that NPs were present in 80-89% of all images.
Boxes with "*" indicate presence of NP in between 20-80% of images.
Blank boxes indicate NP presence in less than 20% of images.

However, when administered in normal saline, PS-PEG NPs were found in the ICS up to 1.0 mm away from the plane of injection (Table 3), and were localized only within PVS at 1.5 mm (Table 3). Furthermore, PS-PEG NPs infused in hyperosmolar 3% saline were found in both the ICS and PVS up to 1.5 mm away (Table 3), indicating that NP distribution in ICS may be enhanced by reducing ECM resistance. Reduced NP accumulation in the PVS and improved NP distribution throughout the ICS achieved by a hyperosmolar infusate solution demonstrates these formulations can be used to overcome a critical limitation of CED.

Figure 3A:
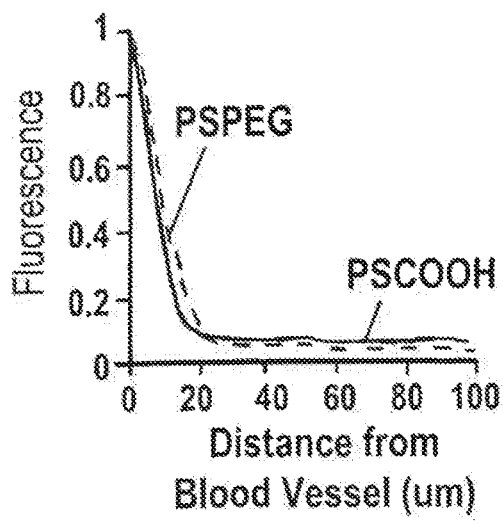
FIGS. 3A-3D are graphs showing the perivascular distribution of nanoparticles following CED.
Figure 3B:
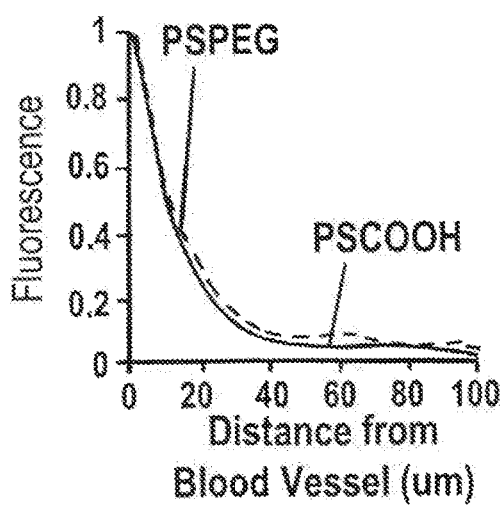
Figure 3C:
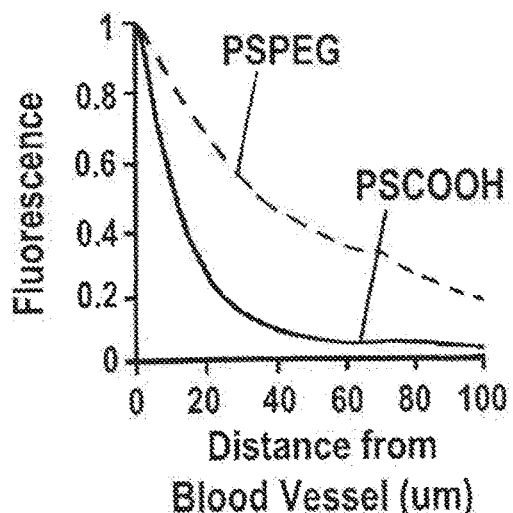
Figure 3D:
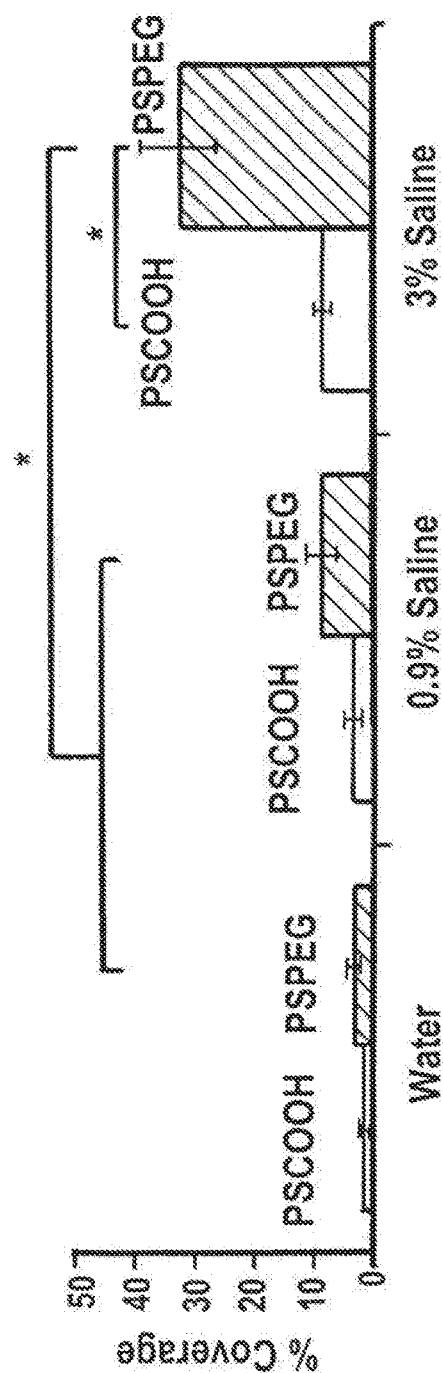

Regardless of the infusate solution, PS-COOH NPs were found solely associated with blood vessels (Table 3). Increasing saline concentration reduced the overall distance that PS-COOHNPs trafficked through PVS. When infused in water and 0.9% saline, PS-COOH NPs were found in PVS up to 1.5 mm away from the plane of administration, whereas PS-COOH NPs infused in 3% saline were located in PVS only up to 0.5 mm away. The reduced distance can be attributed to the instability of PS-COOH NPs in hyperosmolar saline (Table 1) as their rapid aggregation to sizes larger than 1 μm would significantly increase the hindrances encountered when trafficking through the PVS of arterioles that are sub-1 μm in width (Patek, P., Anat. Rec., 1944, 88(1), 1-24).

ii. Hyperosmotic Infusate Solution Enables Nanoparticle Escape from Perivascular Spaces Due to the intrinsically lower physical resistance of the PVS compared to that of ICS (Foley, et al., Ann Biomed Eng, 2012, 40(2), 292-303), NP trafficking in the PVS is inevitable regardless of administration parameters or NP characteristics. Furthermore, NP remain sequestered in the PVS, unable to pass through the glia limitans (Zhang, et al., J Anat, 1990, 170, 111-23), a barrier formed by astrocytic endfeet that strictly delineates the PVS from the ICS with only ~20 nm intercellular openings (Iliff, et al., Sci Transl Med, 2012, 4(147), 147ra111; Engelhardt and Coisne, Fluids Barriers CNS, 2011, 8(1), 4; Papadopoulos, et al., FASEB J, 2004, 18(11), 1291-3). It was hypothesized that by modulating the glia limitans using a hyperosmotic infusate solution, NP may be driven to escape PVS and distribute into the ICS. The lateral striate artery, a large blood vessel structure previously shown to significantly sequester NP (Krauze, et al., Exp Neurol, 2005, 196(1), 104-11), was investigated to determine the extent of NP escape from this major artery. When administered in water, both PS-PEG NPs and PS-COOH NPs were confined to PVS; less than 10% of PS-PEG NPs or PS-COOH NPs fluorescence was detected at a distance of 20 μm from the blood vessel (FIG. 3A). Similarly, when administered in 0.9% saline, only 20% of both PS-PEG NPs and PS-COOH NPs fluorescence was observed at a distance of 20 μm (FIG. 3B), indicating that even with non-adhesive coatings, NPs fail to traverse the glia limitans into the ICS. But when particles were infused in hyperosmolar 3% saline, while PS-COOH NPs were similarly sequestered in PVS, PS-PEG NPs exhibited markedly improved escape from PVS (FIG. 3C), indicating that a combination of a hyperosmolar solution with non-adhesive NP is necessary for PVS escape. In fact, 65% of PS-PEG NPs fluorescence was observed at a distance of 20 μm with 20% of the fluorescence detectable even at 100 μm. In these same high-resolution lateral striate artery images, the percent coverage of fluorescent NP outside the PVS and within the brain ICS was determined. Fluorescence of PS-PEG administered in 3% saline was detected across 30% of the ICS in the image, a significantly higher coverage (P<0.05) as compared to PS-PEG administered in 0.9% saline (8% coverage) and water (3% coverage) (FIG. 3D).

The migration of non-adhesive NP from the PVS into the ICS following infusion in a hyperosmolar solution can likely be attributed to the disruption and enlargement of the 20 nm astrocytic intercellular clefts, similar to our prior modulation of the brain ECM pores. Thus, larger NP can then escape into the ICS, but only if the NP surface is rendered non-adhesive. Regardless of the infusate solution, conventional NP are unable to reenter the brain ICS due to their adhesive nature that confines them to the PVS. To date, only small molecules (i.e. water, alexafluor dyes, small dextrans) and 20 nm adeno-associated viruses (AAV) have been shown to partition from the PVS into the ICS (Salegio, et al., Front Neuroanat, 2014, 8, 9; Iliff, et al., Sci Transl Med, 2012, 4(147), 147ra111). The delivery of NP therapeutics as large as 60 nm in diameter out of PVS, through the glia limitans, and into the ICS has now been demonstrated.

iii. Delivery Strategies Successfully Applied to Other Drug Nanocarrier Systems

The studies based on model NP probes can be translated to therapeutic NP derived from poly(lactic-co-glycolic acid) (PLGA), a commonly utilized FDA-approved polymer for delivering a variety of drugs (Bala, et al., Crit Rev Ther Drug Carrier Syst, 2004, 21(5), 387-422). The sizes of PLGA-based NP in iso-osmolar and hyperosmolar saline solutions were characterized. Uncoated PLGA NP were 80 nm upon formulation, but were highly unstable and rapidly aggregated in 3% saline (Table 4).

TABLE 4

Sizes of PLGA and PLGA-PEG NP in iso-osmolar, or hyperosmolar saline solutions.

| Particle type | PEG wt % | Size in 10 mM NaCl (nm) | Size in 0.9% saline (nm) | Size in 3% saline (nm) |
|---|---|---|---|---|
| PLGA | 0 | 80 ± 1 | 97 ± 13 | 1377 ± 224 |
| PLGA-PEG | 25 | 71 ± 1 | 75 ± 1 | 75 ± 3 |

Figure 4A:
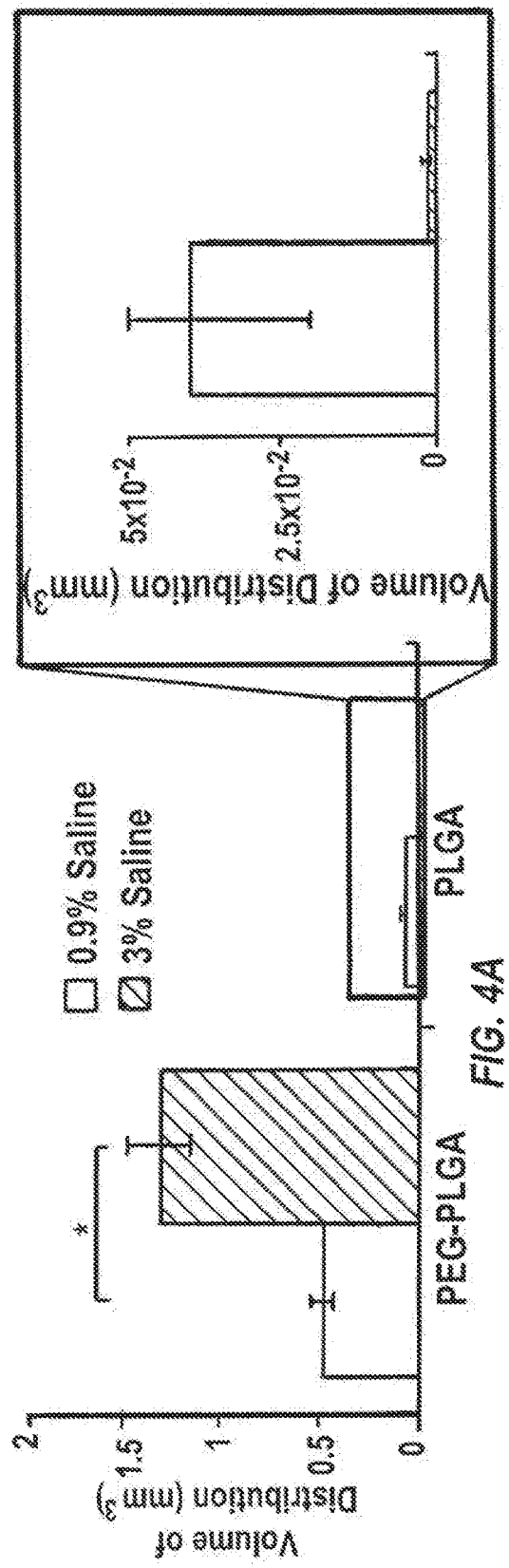
FIGS. 4A-4C are graphs showing the in vivo distribution of therapeutic PLGA-based NP in mouse striatum administered via CED.
Figure 4B:
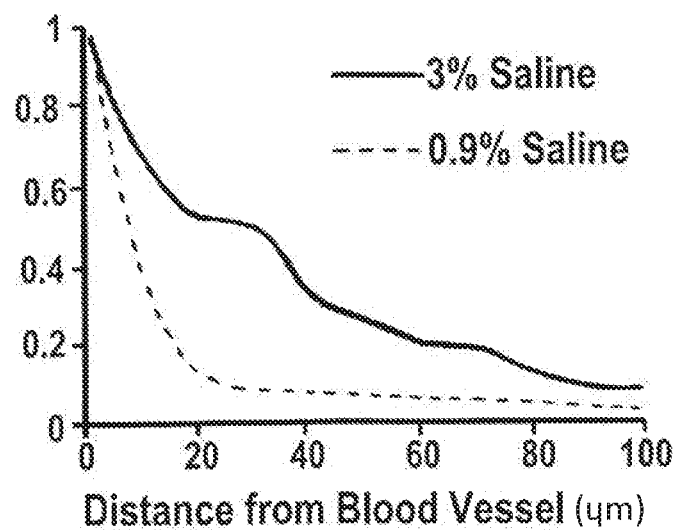
Figure 4C:
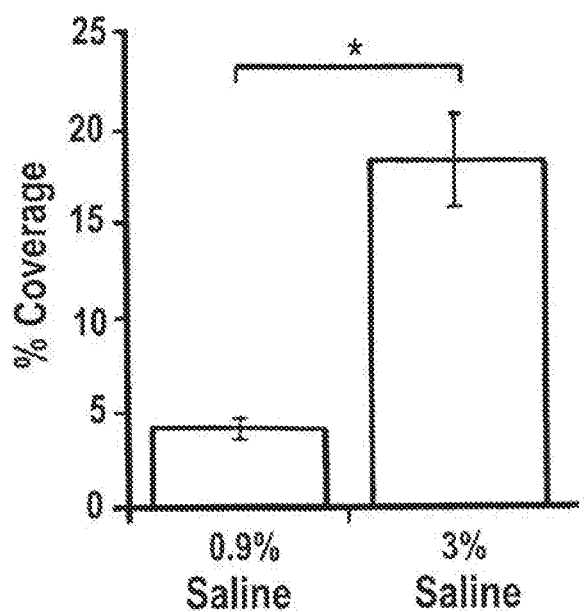

Non-adhesive PLGA-PEG NP 71 nm in diameter following formulation remained stable in higher saline concentrations. Following in vivo CED administration, fluorescence based quantification of NP distribution yielded a statistically significant improvement in the distribution of PLGA-PEG NP as compared to its PLGA counterpart in both 0.9% saline and 3% saline. Additionally, Vd of PLGA-PEG when administered in 3% saline was 2.7-fold than the Vd of PLGA-PEG administered in 0.9% saline (FIG. 4A). Extensive PLGA-PEG distribution throughout the brain interstitium led to perivascular distribution along lateral striate arteries whereas unmodified PLGA NP remained localized to the point of administration. In good agreement with the observations with probe particles (FIG. 3C), it was found that PLGA-PEG NP could escape PVS when administered in hyperosmolar 3% saline (FIG. 4B). At a distance of 20 μm from the blood vessel, 52% and 12% of PLGA-PEG fluorescence was detected when administered in 3% saline and 0.9% saline, respectively. Furthermore, the percent coverage of PLGA-PEG within the brain ICS following administration in 3% saline was significantly higher than PLGA-PEG administered in 0.9% saline (FIG. 4C, P<0.05). Lastly, animals sacrificed either 1 hour or 72 hours post-administration, showed no significant cellular toxicity or inflammation in the vicinity of the implanted catheter at either timepoint indicating limited acute or chronic toxicities. All animals exhibited normal behavior up to 72 hours post administration. These results validate the findings with probe NP that the combined use of non-adhesive surface coatings and hyperosmolar infusate solution is required to maximize the distribution of NP as well as their drug payloads following CED. Therefore administering a therapeutic, non-adhesive biodegradable NP using an appropriate hyperosmolar infusate solution should enhance therapeutic distribution and further improve therapeutic efficacy.

In conclusion, a delivery strategy that focuses on maximizing NP distribution in the brain has been developed which overcomes the hindrances of brain ECM components and preferable NP trafficking and sequestration within PVS by administering non-adhesive NP using CED in a hyperosmolar infusate solution, and is able to address major drawbacks currently associated with CED in both the preclinical and clinical settings for treatment of neurological diseases.

We claim:

1. A composition for delivery of nanoparticles to tissues including brain, the composition comprising
   (i) a hyperosmolar solution for a tissue to which it is to be administered having a salt concentration between 1% and 10% NaCl; and
   (ii) nanoparticles comprising
      a first polymer selected from the group consisting of poly(hydroxy acids), polyanhydrides, poly(ortho)esters, polyurethanes, polyesters, poly(amine-co-ester), polyhydroxyalkanoates, blends and copolymers thereof, and
         a second hydrophilic, neutrally charged polyalkylene glycol polymer, covalently linked to the first polymer to form a polymer conjugate,
      wherein the second hydrophilic and neutrally charged polymer forms a coating on the surface of the nanoparticles and the first polymer forms the core of the nanoparticles,
      wherein the concentration of the hyperosmolar solution and the density of the hydrophilic, neutrally charged polymer in the surface coating are in amounts effective to enhance the diffusion and distribution of the nanoparticles within tissues, and
      wherein the density of the hydrophilic, neutrally charged polyalkylene glycol polymer on the surface of the nanoparticles is at least 0.01 units/nm$^2$.

2. The composition of claim 1, for delivery into the brain parenchyma.

3. The composition of claim 1, wherein the nanoparticles have a diameter of less than or equal to 114 nm, 80 nm, or 60 nm.

4. The composition of claim 1, wherein the second hydrophilic polymer is selected from the group consisting of polyethylene glycol, polysorbate 80, polyethylene glycol-polyoxyethylene, and combinations thereof.

5. The composition of claim 4, wherein the second hydrophilic polymer is polyethylene glycol having a molecular weight between 1,000 Daltons and 10,000 Daltons.

6. The composition of claim 5, wherein the polyethylene glycol has a molecular weight of 5,000 Daltons.

7. The composition of claim 6, wherein the first polymer is selected from the group consisting of poly(hydroxy acids), polyanhydrides, poly(ortho)esters, polyhydroxyalkanoates, blends and copolymers thereof.

8. The composition of claim 7, wherein the poly(hydroxy acid) is poly(lactide-co-glycolic acid).

9. The composition of claim 1, wherein the concentration of the sodium chloride in the saline solution is 3%.

10. The composition of claim 1, wherein the weight percent of the second hydrophilic polymer relative to total nanoparticle is at least 80%.

11. The composition of claim 1, wherein the weight percent of the second hydrophilic polymer relative to the weight of the polymer conjugate is at least 25%.

12. A dosage formulation for delivery of a therapeutic, prophylactic or diagnostic agent to the brain, consisting of
   an effective amount of the compositions of claim 1 for administration to the brain.

13. The formulation of claim 12, wherein the compositions are formulated for direct administration to the brain using convection enhanced delivery.

14. A method for treating one or more symptoms of a disease or disorder of the brain, comprising administering to the brain a formulation comprising
   a therapeutically effective amount of the composition of claim 1.

15. The method of claim 14, wherein the formulation is administered to the brain using convection enhanced delivery.

16. The method of claim 15, wherein the composition is administered in combination with one or more techniques to facilitate passage of the particles through the blood brain barrier.

* * * * *

UNITED STATES PATENT AND TRADEMARK OFFICE
CERTIFICATE OF CORRECTION

PATENT NO. : 10,632,080 B2
APPLICATION NO. : 15/759465
DATED : April 28, 2020
INVENTOR(S) : Clark Zhang et al.

Page 1 of 1

It is certified that error appears in the above-identified patent and that said Letters Patent is hereby corrected as shown below:

In the Specification

Column 1, Lines 17-19, replace "This invention was made with government support under CA164789 awarded by the National Institutes of Health. The government has certain rights in the invention." with "This invention was made with government support under CA164789 and EY001765 awarded by the National Institutes of Health. The government has certain rights in the invention."

Signed and Sealed this
Ninth Day of June, 2020

Andrei Iancu
*Director of the United States Patent and Trademark Office*